(12) United States Patent
de Juan et al.

(10) Patent No.: US 12,360,350 B2
(45) Date of Patent: Jul. 15, 2025

(54) DEVICES, SYSTEMS, AND METHODS FOR OTOLOGY

(71) Applicant: Spiral Therapeutics Inc., Brisbane, CA (US)

(72) Inventors: Eugene de Juan, Brisbane, CA (US); Hugo Peris, Brisbane, CA (US); Signe Erickson, Brisbane, CA (US); Vrad Levering, Brisbane, CA (US); Nikhil Talreja, Brisbane (CA)

(73) Assignee: Spiral Therapeutics, Inc., South San Francisco, CA (US)

( * ) Notice: Subject to any disclaimer, the term of this patent is extended or adjusted under 35 U.S.C. 154(b) by 888 days.

(21) Appl. No.: 17/155,585

(22) Filed: Jan. 22, 2021

(65) Prior Publication Data
US 2021/0228412 A1 Jul. 29, 2021

Related U.S. Application Data

(60) Provisional application No. 63/082,996, filed on Sep. 24, 2020, provisional application No. 63/081,015,
(Continued)

(51) Int. Cl.
*G02B 21/00* (2006.01)
*A61B 1/018* (2006.01)
(Continued)

(52) U.S. Cl.
CPC .......... *G02B 21/0012* (2013.01); *A61B 1/018* (2013.01); *A61B 1/227* (2013.01);
(Continued)

(58) Field of Classification Search
CPC .......... A61B 2017/00787; A61B 2018/00327; A61B 17/32; A61B 1/227; A61B 17/3423;
(Continued)

(56) References Cited

U.S. PATENT DOCUMENTS 5,421,818 A 6/1995 Arenberg
5,707,383 A 1/1998 Bays et al.
(Continued)

FOREIGN PATENT DOCUMENTS

JP 2001-508033 A 6/2001
JP 2009-536666 A 10/2009
(Continued)

OTHER PUBLICATIONS

Smooth muscle in the annulus fibrosus of the tympanic membrane in bats, rodents, insectivores, and humans (Year: 2005).*
(Continued)

*Primary Examiner* — Katherine H Schwiker
*Assistant Examiner* — Zehra Jaffri
(74) *Attorney, Agent, or Firm* — Fish & Richardson P.C.

(57) ABSTRACT

Devices, systems, and methods can be employed to facilitate performing procedures in the outer, middle, and/or inner ear in order to diagnose and/or treat disorders including, but not limited to, hearing loss and other ear disorders. For example, this document describes devices, systems and methods that include instruments and techniques to minimize the invasiveness and/or to enhance the efficacy of procedures that are performed in the outer, middle, and/or inner ear spaces such as mastoidectomy, tympanoplasty, cholesteatoma treatments, otosclerosis treatments, and Eustachian tube treatments.

10 Claims, 14 Drawing Sheets

Related U.S. Application Data filed on Sep. 21, 2020, provisional application No. 63/080,510, filed on Sep. 18, 2020, provisional application No. 63/078,141, filed on Sep. 14, 2020, provisional application No. 63/077,448, filed on Sep. 11, 2020, provisional application No. 63/051,568, filed on Jul. 14, 2020, provisional application No. 63/040,495, filed on Jun. 17, 2020, provisional application No. 63/024,183, filed on May 13, 2020, provisional application No. 62/965,481, filed on Jan. 24, 2020.

(51) Int. Cl.
| | |
|---|---|
| A61B 1/227 | (2006.01) |
| A61B 17/00 | (2006.01) |
| A61B 17/29 | (2006.01) |
| A61B 17/32 | (2006.01) |
| A61B 17/3205 | (2006.01) |
| A61B 17/34 | (2006.01) |
| A61B 18/00 | (2006.01) |
| A61B 18/04 | (2006.01) |
| A61B 18/14 | (2006.01) |
| A61B 18/20 | (2006.01) |
| A61F 2/18 | (2006.01) |
| A61F 2/958 | (2013.01) |
| A61F 11/20 | (2022.01) |
| A61M 31/00 | (2006.01) |
| A61M 37/00 | (2006.01) |
| G02B 21/22 | (2006.01) |

(52) U.S. Cl.
CPC ...... *A61B 17/29* (2013.01); *A61B 17/320068* (2013.01); *A61B 17/3205* (2013.01); *A61B 17/3423* (2013.01); *A61B 17/3468* (2013.01); *A61B 17/3478* (2013.01); *A61B 18/04* (2013.01); *A61B 18/1485* (2013.01); *A61B 18/20* (2013.01); *A61F 2/958* (2013.01); *A61F 11/20* (2022.01); *A61F 11/202* (2022.01); *A61M 31/00* (2013.01); *A61M 31/002* (2013.01); *A61M 37/0015* (2013.01); *G02B 21/0032* (2013.01); *G02B 21/22* (2013.01); *A61B 2017/00115* (2013.01); *A61B 2017/00787* (2013.01); *A61B 2017/00867* (2013.01); *A61B 2017/32007* (2017.08); *A61B 2018/00327* (2013.01); *A61B 2217/005* (2013.01); *A61F 2002/183* (2013.01); *A61F 2250/0067* (2013.01); *A61M 2037/0023* (2013.01); *A61M 2037/0046* (2013.01); *A61M 2205/04* (2013.01); *A61M 2210/0662* (2013.01); *A61M 2210/0668* (2013.01)

(58) Field of Classification Search
CPC ... A61B 17/3478; A61B 17/345; A61F 11/00; A61F 11/20; A61F 2/18; A61F 2002/183; A51B 17/24; A61M 2210/0662; A61M 2210/0668

See application file for complete search history.

(56) References Cited

U.S. PATENT DOCUMENTS

| | | | |
|---|---|---|---|
| 5,849,008 | A | 12/1998 | Anthony |
| 6,024,726 | A | 2/2000 | Hill |
| 6,045,528 | A | 4/2000 | Arenberg et al. |
| 6,093,150 | A * | 7/2000 | Chandler .............. A61B 8/12 600/459 |
| 6,120,484 | A | 9/2000 | Silverstein |
| 6,440,102 | B1 | 8/2002 | Arenberg et al. |
| 6,475,138 | B1 * | 11/2002 | Schechter ............ A61B 18/20 606/17 |
| 6,648,873 | B2 | 11/2003 | Arenberg et al. |
| 7,351,246 | B2 | 4/2008 | Epley |
| 7,704,259 | B2 | 4/2010 | Kaplan et al. |
| 8,197,461 | B1 | 6/2012 | Arenberg et al. |
| 9,352,084 | B2 | 5/2016 | Decker et al. |
| 9,616,207 | B2 | 4/2017 | Verhoeven |
| 10,130,514 | B2 | 11/2018 | Imran et al. |
| 2003/0220536 | A1 | 11/2003 | Hissong |
| 2004/0172005 | A1 | 9/2004 | Arenberg et al. |
| 2005/0182385 | A1 * | 8/2005 | Epley ................. A61M 5/14244 604/514 |
| 2007/0264296 | A1 | 11/2007 | Myntti |
| 2008/0154343 | A1 * | 6/2008 | Li .......................... A61B 18/22 600/101 |
| 2011/0224629 | A1 | 9/2011 | Jolly et al. |
| 2013/0211438 | A1 | 8/2013 | Dubois et al. |
| 2013/0245569 | A1 | 9/2013 | Jolly et al. |
| 2013/0274715 | A1 | 10/2013 | Chan et al. |
| 2015/0151095 | A1 * | 6/2015 | Tarabichi ............ A61M 29/02 606/192 |
| 2016/0346511 | A1 | 12/2016 | Cohen et al. |
| 2017/0071509 | A1 * | 3/2017 | Pandey ................. A61B 5/0075 |
| 2017/0172804 | A1 | 6/2017 | Watanabe et al. |
| 2017/0252089 | A1 | 9/2017 | Hester et al. |
| 2019/0015254 | A1 | 1/2019 | Bendory et al. |
| 2019/0321610 | A1 | 10/2019 | Goldfarb et al. |
| 2019/0321611 | A1 | 10/2019 | Sacherman et al. |
| 2020/0094030 | A1 | 3/2020 | Kim et al. |
| 2021/0128457 | A1 * | 5/2021 | Liao ................... A61K 47/6925 |

FOREIGN PATENT DOCUMENTS

| | | | | |
|---|---|---|---|---|
| JP | | 2015-109990 A | 6/2015 | |
| WO | WO | 2007/134055 A1 | 11/2007 | |
| WO | WO | 2008/097317 | 8/2008 | |
| WO | WO | 2019/152866 | 8/2019 | |
| WO | WO | 2019/200529 | 10/2019 | |
| WO | | WO-2019200259 A1 * | 10/2019 | ......... A61B 1/00119 |
| WO | WO | 2020/115674 | 6/2020 | |

OTHER PUBLICATIONS

Cholesteatoma in children, predictors and calculation of recurrence rates (Year: 1999).*
Neuroradiology of Cholesteatomas (Year: 2011).*
International Search Report and Written Opinion in International Appln. No. PCT/US2021/14610, dated Jun. 30, 2021, 11 pages.
Extended European Search Report in European Appln No. 21744191.4, dated Jan. 23, 2024, 8 pages.

\* cited by examiner

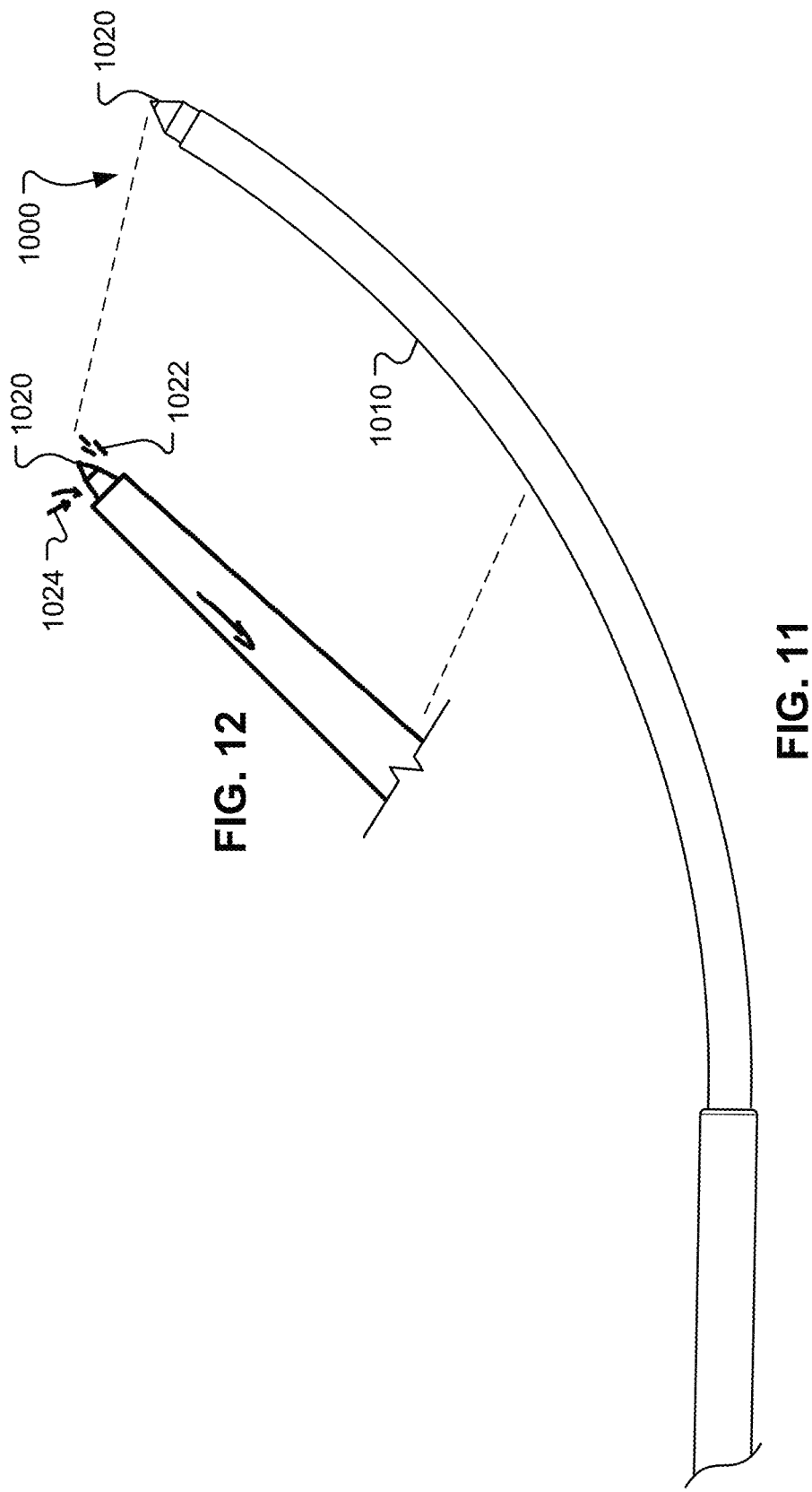

CROSS-SECTIONAL VIEW A--A

ALTERNATIVE CROSS-SECTIONAL VIEW A--A

DEVICES, SYSTEMS, AND METHODS FOR OTOLOGY

CROSS-REFERENCE TO RELATED APPLICATIONS

This application claims the benefit of priority to U.S. Provisional Application No. 62/965,481 filed on Jan. 24, 2020, U.S. Provisional Application No. 63/024,183 filed on May 13, 2020 (which is fully incorporated herein by reference), U.S. Provisional Application No. 63/040,495 filed on Jun. 17, 2020 (which is fully incorporated herein by reference), U.S. Provisional Application No. 63/051,568 filed on Jul. 14, 2020 (which is fully incorporated herein by reference), U.S. Provisional Application No. 63/077,448 filed on Sep. 11, 2020 (which is fully incorporated herein by reference), U.S. Provisional Application No. 63/078,141 filed on Sep. 14, 2020 (which is fully incorporated herein by reference), U.S. Provisional Application No. 63/080,510 filed on Sep. 18, 2020 (which is fully incorporated herein by reference), U.S. Provisional Application No. 63/081,015 filed on Sep. 21, 2020 (which is fully incorporated herein by reference), and U.S. Provisional Application No. 63/082,996 filed on Sep. 24, 2020 (which is fully incorporated herein by reference).

TECHNICAL FIELD

This document relates to devices, systems, and methods for facilitating procedures in the outer, middle, and inner ear in order to diagnose and/or treat disorders including, but not limited to, hearing loss and other ear disorders. In some examples, the systems and methods include instruments and techniques that can be used to minimize the invasiveness of procedures performed in the outer, middle, and/or inner ear spaces.

BACKGROUND

The human ear is subject to a variety of disorders including, but not limited to, hearing loss, tinnitus, balance disorders including vertigo, Meniere's Disease, vestibular neuronitis, vestibular schwannoma, labyrinthitis, otosclerosis, ossicular chain dislocation, cholesteatoma, outer ear infections, middle ear infections, and tympanic membrane perforations, to provide a few examples.

In one example, Conductive Hearing Loss (CHL) involves the loss of normal mechanical pathways for sound to reach the hair cells in the cochlea, for example due to malformation, accumulation of fluid in the middle ear, disruption of the tympanic membrane, presence of tumors, and/or damage to ossicles. Sensorineural Hearing Loss (SNHL) is due to the absence of, or damage to, hair cells in the cochlea, or to impairment of downstream neural signaling. SNHL is typically associated with exposure to loud noise, head trauma, aging, infection, Meniere's Disease, tumors, ototoxicity, genetic diseases like Usher Syndrome, and the like.

SUMMARY

This document describes devices, systems, and methods for uses such as, but not limited to, performing procedures in the outer, middle, and/or inner ear in order to diagnose and/or treat disorders including, but not limited to, hearing loss and other ear disorders. For example, this document describes devices, systems and methods that include instruments and techniques to minimize the invasiveness and/or to enhance the efficacy of procedures performed in the outer, middle, and/or inner ear spaces.

In some embodiments the devices, systems, and methods for facilitating procedures described herein can be used for middle ear and/or inner ear procedures which involve surgical access via approaches including (but not limited to) trans-mastoid, trans-canal, endaural, retroaural, postaural, and others. For example, techniques and instruments are described herein for performing trans-mastoid access to the middle ear space with reduced levels of invasiveness. In another example, this disclosure describes instruments and techniques for debulking of cholesteatomas in a minimally invasive manner. In addition, enhanced instruments and techniques for procedures such as tympanoplasty and myringotomy are described herein. Moreover, the devices, systems, and methods described herein are well-suited for use in other cavities or spaces in the body and other approaches, in addition to middle ear and/or inner ear visualization. For example, the devices, systems, and methods are well-suited for visualization and procedures pertaining to the Eustachian tube, mastoid antrum space, and epitympanum, among others.

The devices, systems, and methods described herein can be used in conjunction with additional treatment techniques. For example, the devices, systems, and methods described herein can be used in conjunction with treatment techniques such as, but not limited to, therapeutic agent delivery (which can be in the form of a gel, liquid, or solid), antibiotic delivery, gene delivery, device or implant delivery, diagnostic procedures, and surgical procedures, among others.

In one aspect, this disclosure is directed to a method for treating cholesteatoma or a soft tissue lesion in a middle ear. The method includes advancing, via an outer ear canal, a shaft of an instrument such that a distal tip of the instrument comes into contact with the cholesteatoma or the soft tissue lesion in the middle ear. The method also includes delivering a therapeutic treatment from the instrument to the cholesteatoma or the soft tissue lesion to de-bulk the cholesteatoma or the soft tissue lesion.

Such a method for treating cholesteatoma or a soft tissue lesion in a middle ear may optionally include one or more of the following features. The advancing may include passing the shaft of the instrument through a perforation in a tympanic membrane positioned between the outer ear canal and the middle ear. The method may also include placing a port device in the perforation. The advancing may include passing the shaft of the instrument through a lumen of the port device while the port device is in the perforation. The instrument may be an injector instrument. The delivering the therapeutic treatment may include injecting an agent into the cholesteatoma or the soft tissue lesion from the injector instrument. The instrument may be an ultrasonic instrument. The delivering the therapeutic treatment may include applying ultrasonic energy to the cholesteatoma or the soft tissue lesion from the ultrasonic instrument to emulsify at least a portion of the cholesteatoma or the soft tissue lesion. The instrument may be a laser instrument. The delivering the therapeutic treatment may include applying laser energy to the cholesteatoma or the soft tissue lesion.

In another aspect, this disclosure is directed to a method for removing buildup of ossification around a stapes footplate in a middle ear. The method includes: advancing, via an outer ear canal, a shaft of an instrument such that a distal tip of the instrument is proximate to the buildup of the ossification around the stapes footplate. The method also includes delivering a therapeutic treatment from the instrument to the buildup of the ossification around the stapes footplate to remove at least some of the buildup.

Such a method for removing buildup of ossification around a stapes footplate in a middle ear may optionally include one or more of the following features. The advancing may include passing the shaft of the instrument through a perforation in a tympanic membrane positioned between the outer ear canal and the middle ear. The method may also include placing a port device in the perforation. The advancing may include passing the shaft of the instrument through a lumen of the port device while the port device is in the perforation. The instrument may be a cutting and aspirating instrument. The delivering the therapeutic treatment may include cutting and aspirating some portions of the buildup using the cutting and aspirating instrument. The instrument may be an ultrasonic instrument. The delivering the therapeutic treatment may include applying ultrasonic energy to the buildup from the ultrasonic instrument to emulsify at least a portion of the buildup. The instrument may be a laser instrument. The delivering the therapeutic treatment may include applying laser energy to the buildup from the laser instrument to remove at least a portion of the buildup. The instrument may be a diathermy instrument. The delivering the therapeutic treatment may include applying heat energy to the buildup from the diathermy instrument to remove at least a portion of the buildup.

In another aspect, this disclosure is directed to a method for treating otosclerosis in a middle ear. The method includes advancing, via an outer ear canal, a shaft of an instrument such that a distal tip of the instrument is within the middle ear. The method also includes delivering a therapeutic treatment from the instrument. The instrument can be: (i) a cutting and aspirating instrument, (ii) an ultrasonic instrument, (iii) a laser instrument, or (iv) a diathermy instrument.

In another aspect, this disclosure is directed to a method for resurfacing a periphery of a perforation of a tympanic membrane. The method includes advancing, via an outer ear canal, a shaft of a reciprocating cutting instrument toward the perforation. The method also includes activating the reciprocating cutting instrument to remove tissue from the periphery of the perforation of the tympanic membrane.

Such a method for resurfacing a periphery of a perforation of a tympanic membrane may also include aspirating, by the reciprocating cutting instrument, at least some of the tissue removed from the periphery of the perforation of the tympanic membrane.

In another aspect, this disclosure is directed to another method for resurfacing a periphery of a perforation of a tympanic membrane. The method includes advancing, via an outer ear canal, a shaft of an ultrasonic instrument toward the perforation. The method also includes activating the ultrasonic instrument to remove tissue from the periphery of the perforation of the tympanic membrane.

In another aspect, this disclosure is directed to a method for treating Eustachian tube dysfunction. The method includes: (i) advancing, via an outer ear canal, a shaft of an instrument toward an Eustachian tube, wherein the instrument includes a balloon on a distal end portion of the shaft, wherein the balloon is in a deflated state during the advancing; (ii) positioning the balloon in the Eustachian tube; and (iii) inflating the balloon while the balloon is in the Eustachian tube.

Such a method for treating Eustachian tube dysfunction may optionally include one or more of the following features. The advancing may include passing the shaft of the instrument through a perforation in a tympanic membrane positioned between the outer ear canal and the Eustachian tube. The method may also include placing a port device in the perforation. The advancing may include passing the shaft of the instrument through a lumen of the port device while the port device is in the perforation. The advancing may include passing the shaft of the instrument through an opening of a myringotomy ear drainage tube positioned in a tympanic membrane. In some embodiments, a stent device is positioned on the balloon during the advancing. In some such embodiments, inflating the balloon while the balloon is in the Eustachian tube expands the stent device such that the Eustachian tube is held open by the expanded stent device after removal of the balloon from the Eustachian tube. The stent device may be a drug-eluting stent device.

In another aspect, this disclosure is directed to another method for treating cholesteatoma or a soft tissue lesion in a middle ear. The method includes advancing, via a transmastoid access opening, a shaft of an instrument such that a distal tip of the instrument comes into contact with the cholesteatoma or the soft tissue lesion in the middle ear. The method also includes delivering a therapeutic treatment from the instrument to the cholesteatoma or the soft tissue lesion to de-bulk the cholesteatoma or the soft tissue lesion.

Such a method for treating cholesteatoma or a soft tissue lesion in a middle ear may include one or more of the following optional features. The instrument may be an injector instrument. The delivering the therapeutic treatment may include injecting an agent into the cholesteatoma or the soft tissue lesion from the injector instrument. The instrument may be an ultrasonic instrument. The delivering the therapeutic treatment may include applying ultrasonic energy to the cholesteatoma or the soft tissue lesion from the ultrasonic instrument to emulsify at least a portion of the cholesteatoma or the soft tissue lesion. The instrument may be a laser instrument. The delivering the therapeutic treatment may include applying laser energy to the cholesteatoma or the soft tissue lesion.

Some or all of the embodiments described herein may provide one or more of the following advantages. First, some embodiments of instruments and associated techniques for treating or diagnosing ear disorders as described herein reduce the procedural invasiveness in comparison to conventional methods. For example, instruments and techniques are disclosed for reducing the invasiveness of transmastoid access to the middle and/or inner ear. Accordingly, less mastoid bone removal (mastoidectomy) is necessary. In turn, recovery times, treatment costs, and the potential for complications are all potentially reduced. In another example, debulking of cholesteatomas can be performed in a minimally invasive manner using the instruments and techniques described herein.

Second, the use of the instruments and techniques described herein can enhance the efficacy of various otic procedures. For example, improved tools and methods for debulking cholesteatomas in a minimally-invasive manner are described herein. Such tools include, but are not limited to, ultrasonic instruments, high speed cutting instruments, injector instruments, diathermy instruments, laser instruments, to provide a few examples. In another example, procedures for addressing otosclerosis can be performed with enhanced efficacy using the instruments and techniques described herein. That is the case because, for example, the instruments and techniques described herein can be used with precision to remove buildup while preserving the stapes. In another example, instruments and techniques for reducing procedure time and complication risk in standard stapedectomy and stapedotomy procedures are described. In yet another example, instruments and techniques are described herein for an improved tympanoplasty procedure that can be performed with enhanced efficacy.

Third, new types of otology instruments are described herein, such as instruments for micro-diathermy, pneumatically or electrically driven cutters, suction cutters, micro-suction, ultrasonic cutters/debriders, and so on, and combinations thereof. The specialized instruments and techniques described herein facilitate the performance of new types of therapeutic treatments for inner and middle ear disorders. In addition, current therapeutic treatments can be performed with enhanced efficacy and efficiency using the specialized instruments and techniques described herein.

Fourth, the devices, systems, and methods described herein advantageously allow the ability to pass instruments to the operative field, and to function in fluid-filled spaces in addition to air-filled spaces.

Fifth, methods are described herein for temporarily filling the middle ear and/or outer ear cavities such that treatment procedures can be performed "underwater." This approach confers a number of advantages such as, but not limited to, maintaining fluid equilibrium in the cochlea during surgery, tamponade bleeding, enabling aspiration procedures that allow for constant irrigation or washing of middle ear structures, improving visualization, and enabling the precise use of suction cutters to trim or remove tissues during surgery, and so on, as described herein.

Sixth, the systems described herein can also be used for diagnostic purposes. Such uses can help in procedure planning, changing site of care, and potentially improving patient outcomes.

The details of one or more embodiments of the invention are set forth in the accompanying drawings and the description below. Other features, objects, and advantages of the invention will be apparent from the description and drawings, and from the claims.

DESCRIPTION OF DRAWINGS

FIG. 11 illustrates an example diathermy instrument in accordance with some embodiments.

FIG. 12 illustrates an optional distal tip portion of the diathermy instrument of FIG. 11.

Like reference symbols in the various drawings indicate like elements.

DETAILED DESCRIPTION OF ILLUSTRATIVE EMBODIMENTS

Figure 1:
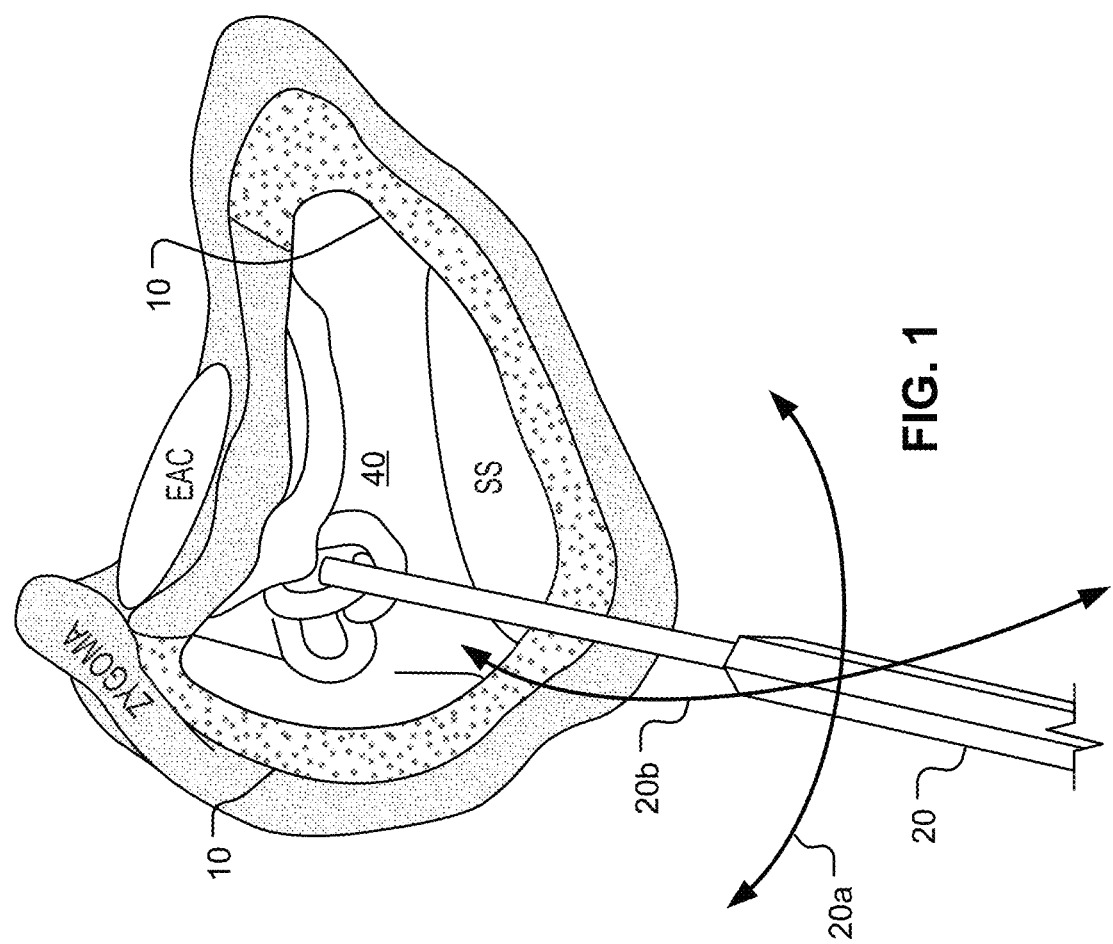
FIG. 1 is a schematic illustration of a conventional trans-mastoid access medical procedure.

Referring now to the schematic illustration of FIG. 1, a conventional trans-mastoid access to a middle ear 40 is depicted. A trans-mastoid approach to the middle ear 40 is used for various otic treatment procedures such as, but not limited to, cholesteatoma removal, labyrinthectomy, placement of cochlear implants, and repair of superior canal dehiscence syndrome, to provide a few examples.

To achieve access to the middle ear 40 using the conventional trans-mastoid approach as depicted, a relatively large amount of cells in the hollow, air-filled spaces in the skull behind the ear within the mastoid bone 10 are removed. Following this simple mastoidectomy, a small opening into the middle ear 40 is created. The amount of bone removed in the initial simple mastoidectomy is driven, at least in part, by the limited reach, maneuverability and size of conventional instruments. Often, even an opening with a small diameter into the middle ear space 40 necessitates a large conical removal of bone 10 surrounding the opening to allow sufficient angles of attack for instruments to the middle ear space 40. As depicted by the arrows 20a and 20b, the instruments 20 are manually maneuvered along substantial paths to avoid delicate and important anatomical structures such as nerves and/or blood vessels during the procedure.

Depending on the extent of the surgery required, additional removal of bone 10 beyond the simple mastoidectomy is often necessary. First, a facial recess may need to be created. Second, in some cases the wall that separates the canal wall and mastoid cavity may need to be removed. Lastly in some cases, the middle ear bones, or ossicles, may need to be removed. The need for additional bone removal beyond a simple mastoidectomy is also driven, at least in part, by the limited reach, maneuverability, and size of conventional instruments (represented here by an instrument 20) used for otic procedures.

Figure 2:
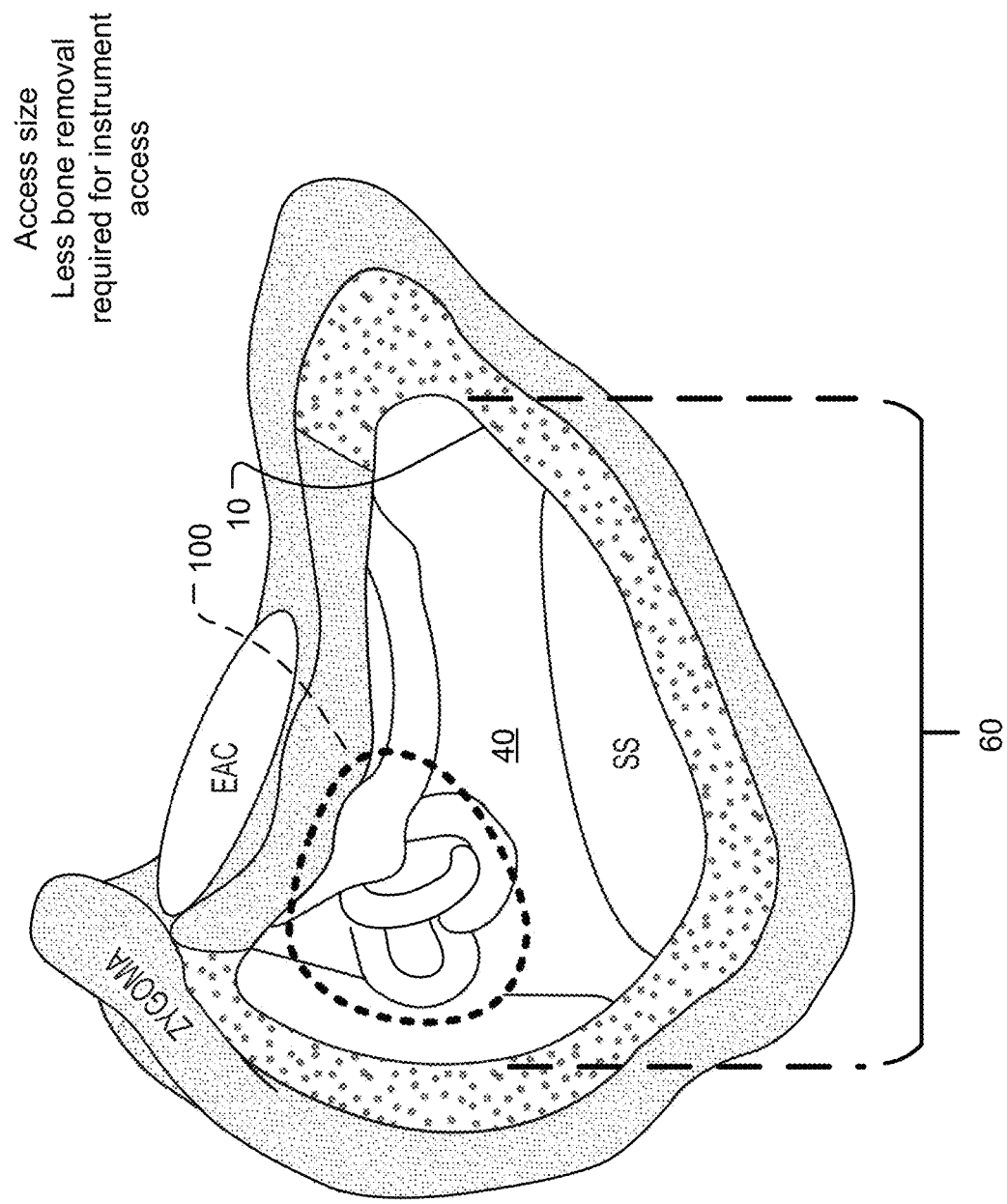
FIG. 2 is a schematic illustration that compares the extents of mastoidectomy associated with conventional trans-mastoid access medical procedures versus the trans-mastoid access medical procedures using the instruments and techniques described herein.

FIG. 2 illustrates a comparison of the conventional simple mastoidectomy 60 associated with a conventional procedure (as illustrated and described above) to the minimal mastoidectomy 100 associated with the trans-mastoid approach using the instruments and techniques described herein. As shown, the minimal mastoidectomy 100 is much smaller. Accordingly, much less mastoid bone 10 removal is necessary for the trans-mastoid approach using the instruments and techniques described herein; due to reducing the diameter of the opening to the middle ear 40 and/or reducing the predominantly conical volume surrounding the opening to the middle ear 40.

The instruments and techniques described herein could be combined with preoperative or intraoperative imaging technologies to further reduce the extent of bone removal required. For example, CT imaging can be used to identify axial access paths for safely drilling to the middle ear cavity 40, circumventing critical structures including the semicircular canals, the sigmoid sinus, the chorda tympani, and the facial nerve. One or more drill paths could then be used to pass small gauge steerable instruments and/or endoscopes into the middle ear cavity 40 through drilled channels along these access paths.

As another potential benefit, the instruments and techniques described herein can help to obviate the need for further bone removal beyond simple mastoidectomy. In particular, the need to perform a canal wall down mastoidectomy can be avoided in many cases. With the conventional, more-invasive canal wall down mastoidectomy, the posterosuperior wall of the external acoustic meatus is removed for increased access to the middle ear 40 and mastoid during surgery. Converting what are typically canal wall down mastoidectomies to canal wall up mastoidectomies that spare the posterosuperior wall of the external acoustic meatus preserves a significant portion of patient anatomy, and also eliminates additional procedural steps associated with grafting and reconstructing the canal wall. In turn, recovery times, treatment costs, and the potential for complications are all potentially reduced. In some cases, the instruments and techniques described herein enable some procedures to be performed entirely through the ear canal, obviating the need for trans-mastoid access altogether. Access can instead be achieved through a variety of trans-canal approaches, even the most invasive of which (where the lifting of the tympanomeatal flap is required) requires minimal or no bone removal for access compared to trans-mastoid approaches.

Figure 3:
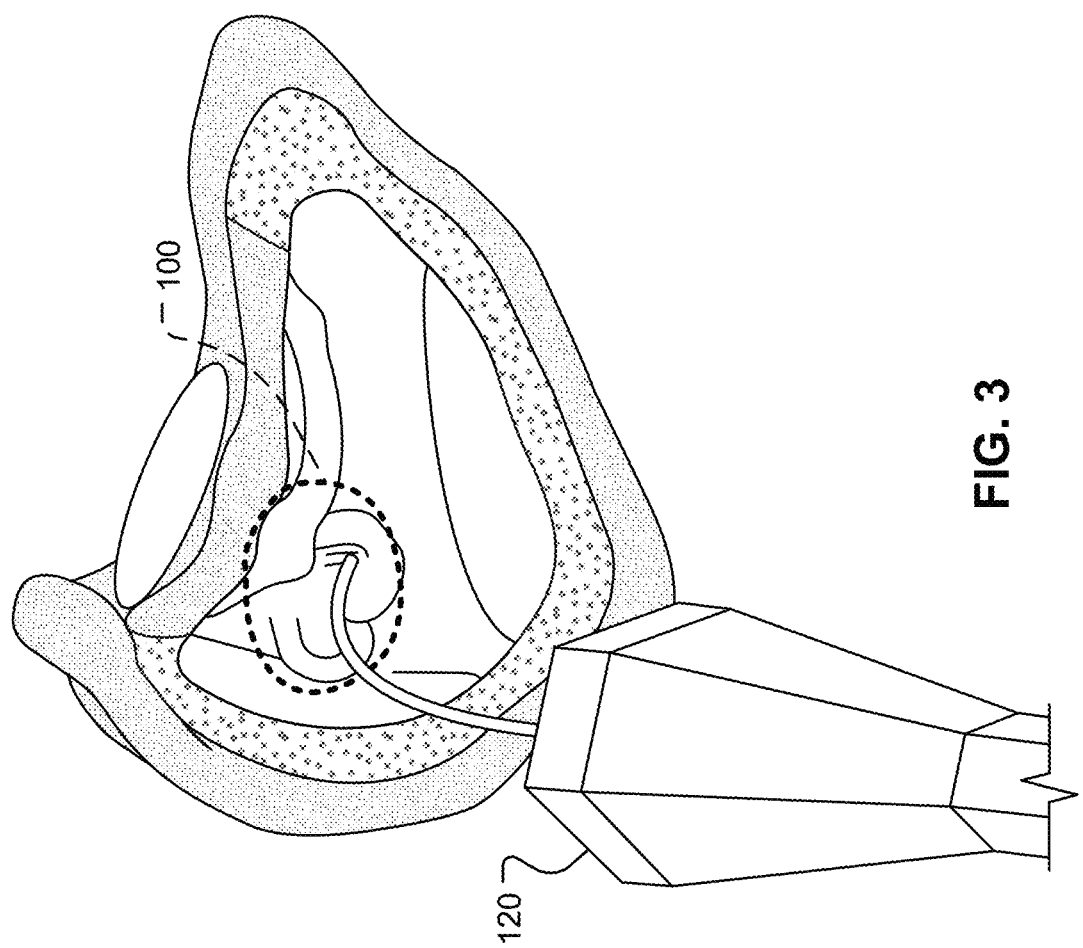
FIG. 3 schematically illustrates the trans-mastoid access medical procedures using the instruments and techniques described

FIG. 3 illustrates an example instrument 120 that is being used to perform the simple minimal mastoidectomy 100 trans-mastoid approach as described herein. The example instrument 120 broadly represents all of the various types of instruments described herein.

As described further below, some of the features of the instruments 120 that facilitate the minimal mastoidectomy 100 trans-mastoid approach include small gauge shafts, flexible shafts, steerable/deflectable shafts, angulated shafts, curved shafts, and the like, and combinations thereof. Moreover, as described further below, the instruments 120 include various types of specialized instruments for high-speed cutting, aspirating, irrigating, diathermy, ultrasound delivery, laser delivery, formulation injection, emulsification, and so on.

Figures 4, 4A, 4B:
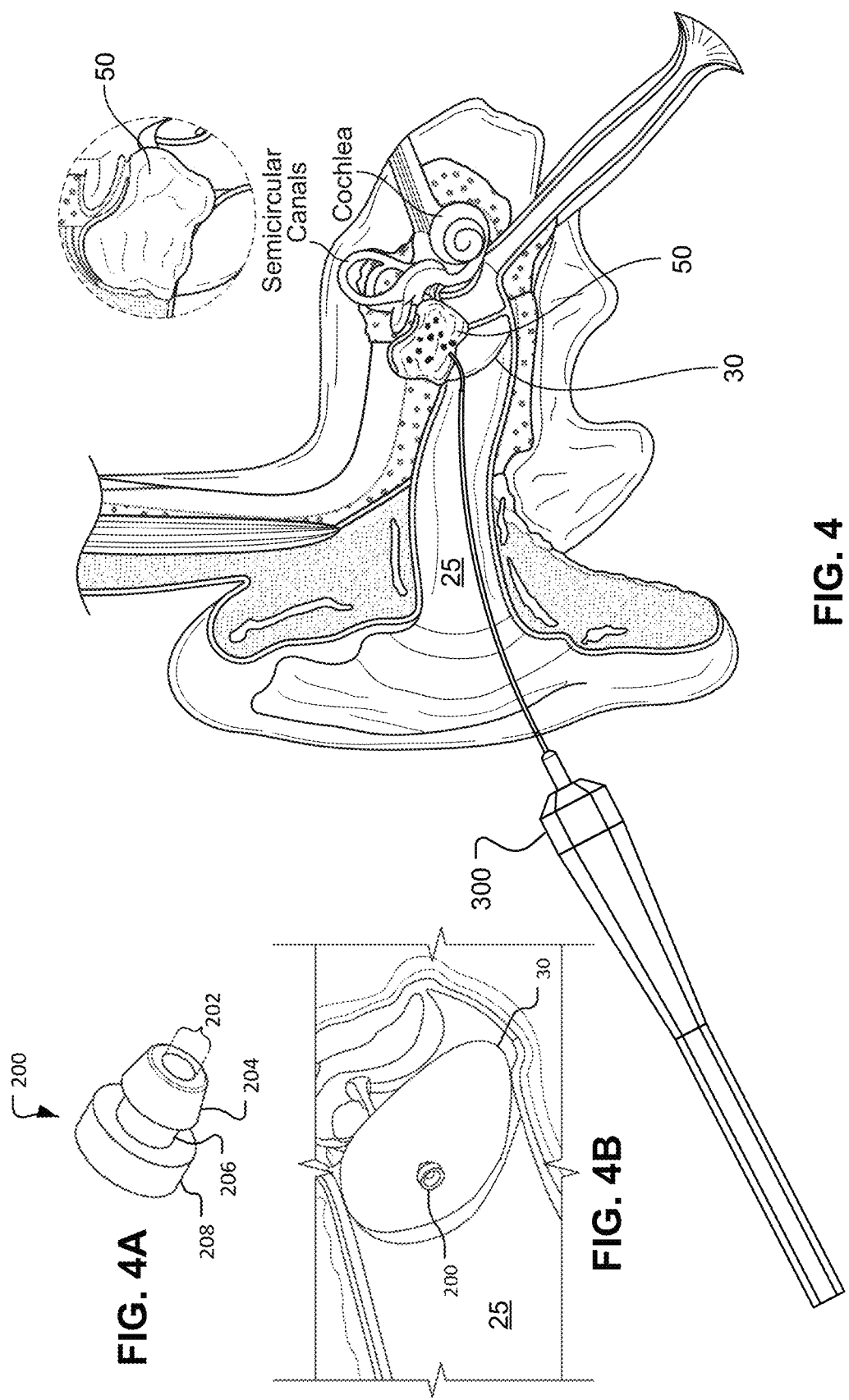
FIG. 4 illustrates an example technique for debulking cholesteatomas in accordance with some embodiments.
FIG. 4A is a perspective view of a tympanic membrane port device that can be used for the technique illustrated in FIG. 4.
FIG. 4B illustrates the tympanic membrane port device of FIG. 4A positioned within a tympanic membrane.

FIG. 4 depicts an example procedure for treating cholesteatoma or soft tissue lesions 50 in accordance with some embodiments. That is, minimally-invasive cholesteatoma or soft tissue lesion debulking can be performed using instruments and techniques described herein.

In the depicted example, an example injector instrument 300 is being used to inject a therapeutic agent into the cholesteatoma 50. In some embodiments, the injected therapeutic agent can be a keratolytic agent (e.g., for breaking down epithelials tissue), an immune response modifier, a cryotherapy agent, and the like, without limitation. Such agents can be administered in combination with surgical approaches to help facilitate tissue removal. Such agents can also be administered after surgical removal to reduce the risk of lesion regrowth. In some cases, these agents can be administered via a sustained release middle ear implant or formulation. The combination of approaches could be uniquely efficacious by combining the benefits of both approaches without substantial increase in risk to patients.

In some cases, the depicted procedure for treating cholesteatoma 50 (or other soft tissue lesion debulking) may be performed periodically, such as every few years, for example. This can be surprisingly beneficial for several reasons. Being able to use minimally invasive visualization allows for the confirmation of cholesteatoma or other lesions much earlier in the disease process (prior to patient reported symptoms), which typically will mean a smaller and less-advanced lesion. Cholesteatoma originates from epithelium at the tympanic membrane or ear canal 25. As it proliferates, it often progresses to involve the ossicles and eventually can invade the mastoid bone, inner ear, facial nerve, or intracranial compartment. The extent of the cholesteatoma dictates the level of invasiveness required for successful removal. Hence early detection and management can minimize the need for more invasive surgical procedures and minimize more severe consequences of the disease, such as erosion of the ossicles requiring prosthetic reconstruction. Additionally, the typical extant procedures have to be so invasive because there is a high level of concern about missing any cholesteatoma, which can regrow and necessitate repeat invasive procedures. Being able to minimally invasively de-bulk the cholesteatoma changes the risk/benefit ratio so that the course of care can both intervene earlier, and more often, which surprisingly carries less risk to the patient overall than one invasive procedure.

While the injection of a therapeutic agent to treat cholesteatoma 50 is depicted, other techniques and associated instruments for treating cholesteatoma 50 can be used and are within the scope of this disclosure. For example, in some embodiments the instrument 300 can be an ultrasonic instrument which can be used to emulsify the cholesteatoma 50. In another example, in some embodiments the instrument 300 can be a high-speed cutting instrument that can physically dissect portions of the cholesteatoma 50. In another example, in some embodiments the instrument 300 can be a diathermy instrument, which would be particularly beneficial in the management of highly vascular glomus tumors to sever feeder vessels and manage intraoperative bleeding. In another example, in some embodiments the instrument 300 can be a laser instrument.

The instruments 300 can include a small gauge shaft, a flexible shaft, a steerable/deflectable shaft, an angulated shaft, a curved shaft, and the like, and combinations thereof. The improved reach and visualization provided by these instruments into the middle ear from a canal-based approach allows greater extent of cholesteatoma removal without requiring more invasive access approaches. Moreover, in some embodiments the instruments 300 can have multiple purposes such as combinations of functionalities including, but not limited to, aspiration, lighting, irrigation, endoscopy, diathermy, laser energy delivery, injection, ultrasound emulsification, and so on.

The depicted minimally-invasive procedure for treating cholesteatoma 50 uses a trans-tympanic membrane approach (e.g., through the region of the tympanic membrane 30). In some implementations, the trans-tympanic membrane approach comprises extending the instrument's shaft through an opening (e.g., a puncture, slit, perforation, etc.) in the tympanic membrane (TM) 30. In particular implementations, the depicted minimally-invasive procedure for treating cholesteatoma 50 uses a tympanomeatal flap procedure whereby the instrument's shaft is extended through the ear canal 25 to the cholesteatoma 50 without passing through the TM 30.

In certain implementations, the trans-tympanic membrane approach for the minimally-invasive procedure for treating cholesteatoma 50 comprises extending the instrument's shaft through a tympanic port device 200 (TM port device 200) as shown in FIGS. 4A and 4B. The example TM port device 200 includes three conjoined, contiguous portions: (i) a distal end portion 204, (ii) a middle portion 206, and (iii) a proximal end portion 208. The lumen 202 runs centrally through each of the portions 204/206/208. In some embodiments, the lumen 202 has a diameter in a range of 0.4 mm to 0.6 mm, 0.5 mm to 0.75 mm, or 0.5 mm to 1.0 mm, without limitation.

The inner diameter or lumen of the proximal portion 208 can be tapered to have a larger diameter at the proximal end, creating a funnel shape to facilitate the alignment of instruments as they enter the port device.

The shape of the distal end portion 204 can be frusto-conical. That is, the distal-most end of the distal end portion 204 has a smaller outer diameter than the proximal-most end of the distal end portion 204. The middle portion 206 and the proximal end portion 208 are each cylindrical. The outer diameter of the middle portion 206 is smaller than the outer diameters of each of: (i) the proximal-most end of the distal end portion 204 and (ii) the proximal end portion 208. Accordingly, the middle portion 206 can be considered a "waist region" of the TM port device 200 in this embodiment. The lumen 202 can be conical, cylindrical, oblong, pyramidal, or other shapes, as can the distal end portion 204.

As described further below, the middle portion 206 is where the tissue of the TM 30 will reside (at least primarily) while the TM port device 200 is implanted in the TM 30. The relatively smaller outer diameter of the middle portion 206 (as compared to the outer diameters of adjacent portions of the distal end portion 204 and the proximal end portion 208) will facilitate detainment of the TM port device 200 in the TM 30. In some embodiments, the outer diameter of the middle portion 206 is in a range of 0.25 mm to 0.75 mm, 0.25 mm to 1.0 mm, or 0.5 mm to 1.25 mm, without limitation. The longitudinal length of the middle portion 206 can be in a range of 0.1 mm to 0.3 mm, 0.1 mm to 0.5 mm, or 0.2 mm to 0.6 mm, without limitation. The outer diameter and length of the middle portion 206 is sufficient to receive the thickness of the TM 30 while preventing buckling, tearing, or other forces from being imparted inadvertently on the TM 30 upon insertion of the TM port device 200. In some embodiments, no waist region is included, and frictional fit between the distal section and TM is sufficient to hold the port device in the TM for the duration of a procedure while reducing forces TM is exposed to during port insertion or removal.

In some embodiments, the TM port device 200 can be implanted in the TM 30 without the use of a trocar needle. Instead, an incision in the TM 30 can be made first using a blade, needle, or laser. Then, the TM port device 200 can be implanted in the TM 30 by advancing the TM port device 200 into the incision.

While the TM port device 200 is implanted (or attached, coupled, engaged, etc.), to the TM 30, the TM port device 200 performs as a grommet, a stress relief member to prevent tearing of the TM 30, a middle ear access port, an instrument insertion tunnel, a working channel, and the like.

The TM port device 200 is configured and sized so that its removal from the TM 30 does not necessitate the use of sutures to seal the incision or fenestration formed in the TM 30 during insertion of the TM port device 200. Generally, a self-sealing fenestration through the TM 30 is no greater than about 2.5 mm in length, preferably between about 0.5 mm and 1.5 mm in length. Although the tools and methods described herein provide the advantage of suture-less access to the middle and/or inner ear, this does not preclude a surgeon from applying one or more closure techniques upon removal of the TM port device 200. That is, if the clinician so desires, one or more techniques for closure of the fenestration(s) in the TM 30 can be performed.

The TM port device 200 can be formed of a material having a rigidity and strength to be inserted and removed from the TM 30 while also withstanding stresses that may arise during manipulation of surgical instruments inserted therethrough. In some embodiments, at least a portion of the TM port device 200 is formed of surgical metals such as stainless steel, titanium, platinum, Nitinol, and/or plastics such as polyimide, PEEK, fluoropolymers, silicone, and the like. In some embodiments, the inserted portion of the TM port device 200 can be formed of polyimide (or other rigid or semi-rigid polymers) and have a maximum outer diameter of no more than about 20 gauge (0.8 mm). One or more portions of the TM port device 200 can be coated with, or formed of, a resilient conformable material.

Figure 5:
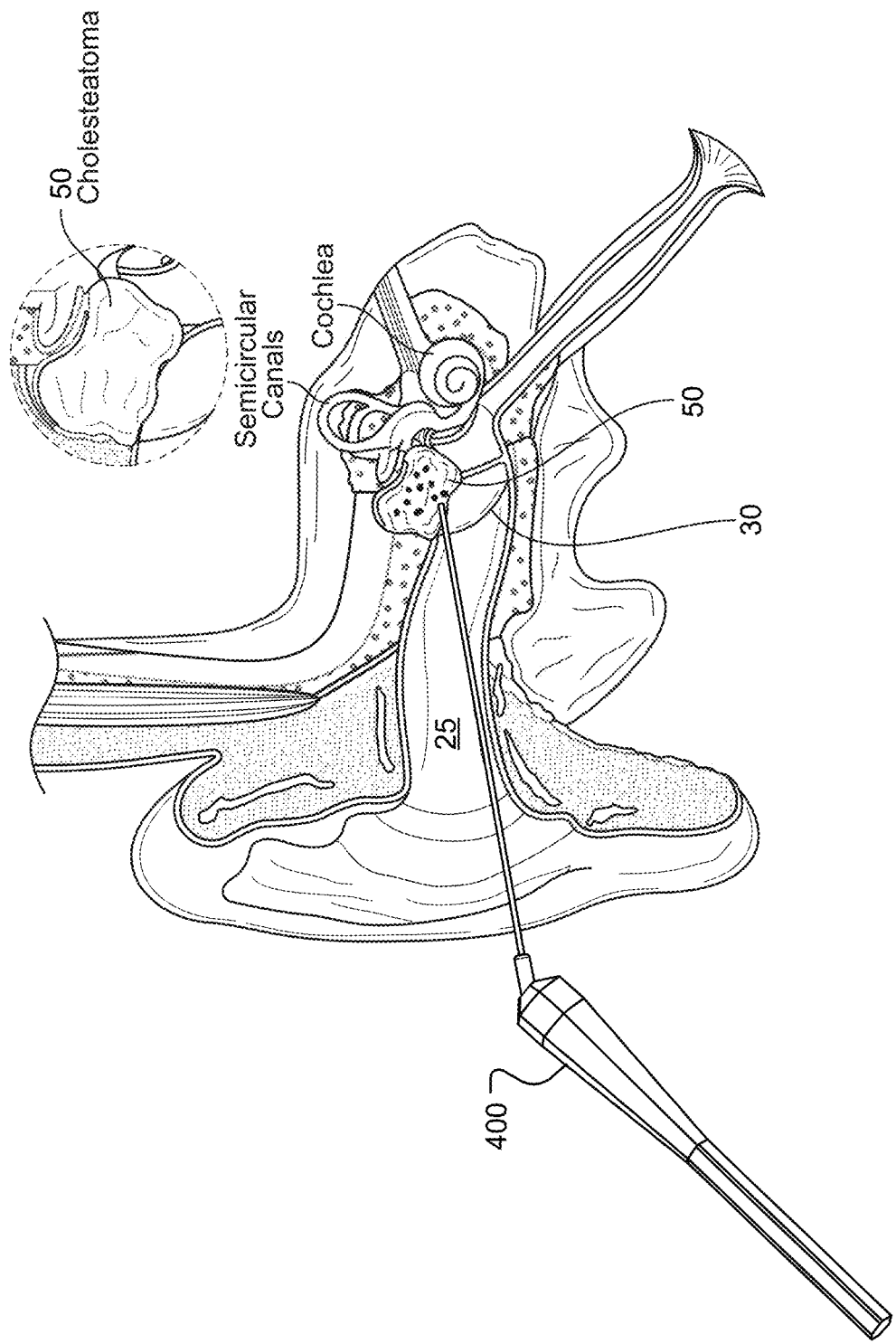
FIG. 5 illustrates another technique for debulking cholesteatomas in accordance with some embodiments.

FIG. 5 depicts another example procedure for treating cholesteatoma 50 in accordance with some embodiments. That is, minimally-invasive cholesteatoma debulking can be performed using instrument 400 and techniques described herein.

For example, in some embodiments the example instrument 400 can be an ultrasonic instrument can be used to emulsify the cholesteatoma 50. In another example, in some embodiments the instrument 400 can be a high-speed cutting instrument that can physically remove portions of the cholesteatoma 50. In yet another example, in some embodiments the instrument 400 can be a diathermy instrument or a laser instrument that can ablate portions of the cholesteatoma 50.

The instruments 400 can include a small gauge shaft, a flexible shaft, a steerable/deflectable shaft, an angulated shaft, a curved shaft, and the like, and combinations thereof. Moreover, in some embodiments the instruments 400 can have multiple purposes such as combinations of functionalities including, but not limited to, aspiration, lighting, irrigation, endoscopy, diathermy, laser energy delivery, injection, ultrasound emulsification, and so on.

In some embodiments, the example instrument 400 for treating cholesteatoma 50 in a minimally-invasive manner can be an ultrasonic instrument, for example. Such an ultrasonic instrument 400 can be used to deliver ultrasonic energy to cause fragmentation, emulsification or resurfacing of tissues such as, but not limited to, membranes, tumors, cholesteatoma, skin, bone, and the like. This technique can be beneficial for controlling bleeding and, in some embodiments, for allowing for the use of aspirating ultrasonic instruments for tissue removal (or aspirating high-speed cutters or diathermy instruments).

In some embodiments, the example instrument 400 can be an ultrasonic instrument that can be used to treat the cholesteatoma 50. An ultrasonic instrument for bone or tissue removal (e.g., cholesteatoma 50) can be combined/incorporated in any of the otologic instruments described herein.

That is, a small gauge ultrasonic instrument equipped with suction and infusion to clear debris could be used to clear small areas of bone adjacent to the facial nerve and other delicate structures. Such an instrument could be used to help debride the bone of soft tissue, as in the case of cholesteatoma 50 removal. The ability of the ultrasonic instrument to be "tuned" to remove specific tissue densities can be highly advantageous for improving the selectivity of tissue removal in cholesteatoma 50 removal.

In some embodiments, the example instrument 400 can be a laser instrument that can be used to treat the cholesteatoma 50. A laser instrument can be combined/incorporated in any of the otologic instruments described herein. Laser-based methods are a useful modality for surgical intervention that is only in limited use currently in otology. Green laser can be particularly useful because it applies heat typically only where there is loose/exposed blood (due to the pigmentation of blood), which allows it to heat and cauterize blood without damaging underlying or adjacent tissue. These instruments have seen limited use in otology for a variety of reasons, including the difficulty in accessing the middle or inner ear region, and because of the bony middle ear structures block straight-line angle of attack to the desired target. In some embodiments, a functional tip laser probe with a tip that can be actuated to generate steerability or functionality off-axis from the adjacent shaft can be highly advantageous and enable a whole new functionality for otologic procedures.

Figure 6:
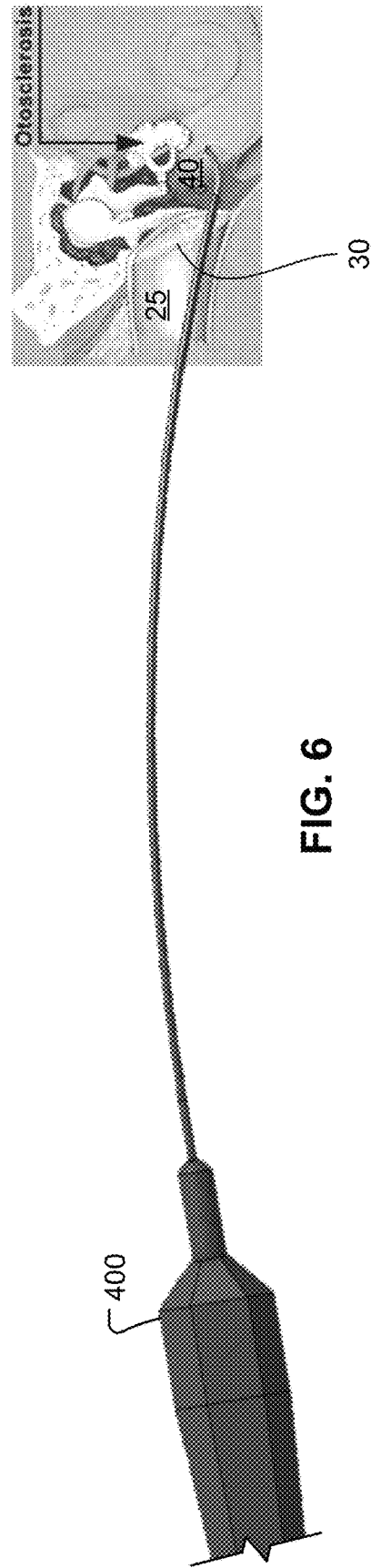
FIG. 6 illustrates an example stapedotomy procedure that can be performed with enhanced efficacy using the instruments and techniques described herein.

FIG. 6 depicts an example minimally-invasive procedure for addressing otosclerosis, thereby replacing current procedures such as stapedectomy and stapedotomy, in accordance with some embodiments. The instruments and techniques for performing the procedure facilitate precise removal of the buildup of ossification around the stapes footplate, known as otosclerosis. Such a procedure would restore mobility of the stapes footplate without having to remove the stapes superstructure and drill the stapes footplate (stapedotomy), or remove the footplate altogether (stapedectomy). The instruments described would allow for precise visualization and access to the stapes footplate, minimizing collateral bone removal and obviating the need for prosthetic reconstruction of the ossicular chain, which is required with current stapedectomy and stapedotomy procedures.

In some embodiments, procedure times and outcomes of standard stapedotomy and stapedectomy procedures could be improved with instruments and techniques described herein. In one example, a side-biting disposable scissors can be used for cutting the stapedius tendon. Typically in stapedotomy and stapedectomy procedures, bone removal at the scutum is required to enable visualization and instrument access. In another example, bone removal can be minimized or avoided with steerable small gauge instruments and widefield visualization systems, which would shorten procedure time and reduce risk of collateral tissue damage. Removal of the scutum is typically performed with a curette, which is difficult to precisely control and presents risk to the adjacent tissues. In yet another example, more precise bone removal could be accomplished with an ultrasonic instrument, thereby reducing risk of damage to adjacent nerves.

Here again, the procedure is depicted as being performed by the example instrument 400 (which is representative of multiple different types of instruments and combinations of instruments, as described herein).

In some cases, the instruments and techniques described herein could enable procedures to be performed minimally invasively through trans-canal 25 and trans-tympanic membrane approaches due to smaller diameter instrumentation and avoiding the need for implants and ossicular bone removal (extant implants and ossicles would likely not fit through minimally invasive access ports or incisions). This would obviate the need for trans-canal 25 approaches such as those requiring the lifting of the tympanomeatal flap, thereby reducing the patient risk and procedure time.

For example, in some embodiments the example instrument 400 for performing the minimally-invasive stapedotomy procedure is a green laser with a steerable tip, aspiration, and lighting. In some embodiments, the example instrument 400 for performing the minimally-invasive stapedotomy procedure is an ultrasonic emulsifier as described above.

The instruments 400 can include a small gauge shaft, a flexible shaft, a steerable/deflectable shaft, an angulated shaft, a curved shaft, and the like, and combinations thereof. Moreover, in some embodiments the instruments 400 can have multiple purposes such as combinations of functionalities including, but not limited to, aspiration, lighting, irrigation, endoscopy, diathermy, laser energy delivery, injection, ultrasound emulsification, and so on.

Figure 14A:
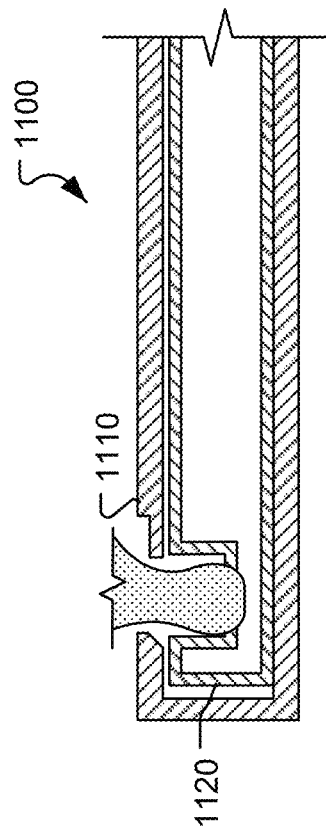
FIGS. 14A-C illustrate the use of the reciprocating cutting instrument of FIG. 14.
Figure 14B:
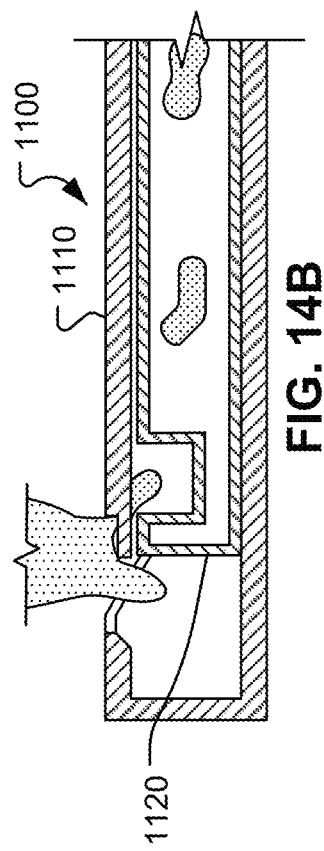
Figure 14C:
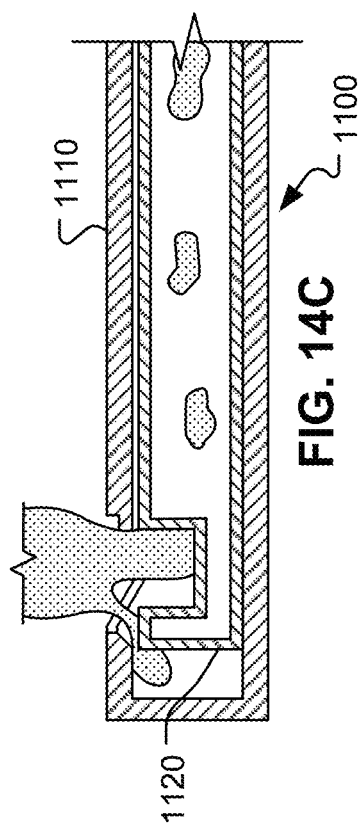
Figure 14:
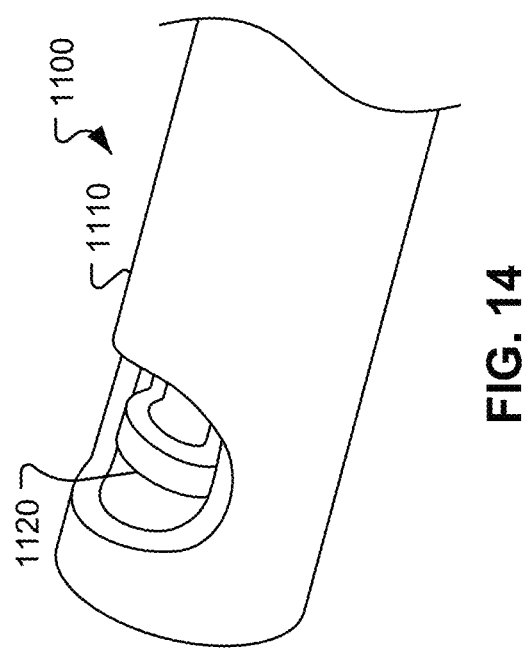
FIG. 14 is a perspective view of an example reciprocating cutting instrument that can be used to perform various procedure described herein.

In some embodiments, the example instrument 400 for performing the minimally-invasive procedure for addressing otosclerosis (FIG. 6) is a high-speed cutting device such as the example pneumatic aspirating cutter 1100 shown in FIG. 14. In some embodiments, the pneumatic aspirating cutter 1100 can be electrically driven (rather than pneumatically driven). The pneumatic aspirating cutter 1100 includes an outer shaft 1110 and an inner reciprocating shaft 1120. The inner reciprocating shaft 1120 reciprocates proximally and distally within the lumen defined by the outer shaft 1110. Accordingly, as depicted in FIGS. 14A-14C tissue can be cut between the outer shaft 1110 and the inner reciprocating shaft 1120 (e.g., like a "guillotine" blade cutter). When portions of tissue are cut, the tissue portions can be aspirated through pneumatic aspirating cutter 1100 as shown.

The pneumatic aspirating cutter 1100 can be useful, for example, for various uses such as stapedotomy, removing middle ear tissue, and resurfacing or freshening the margins of a tympanic membrane perforation in a tympanoplasty procedure (e.g., a tympanic membrane repair procedure, as described further below).

Still also referring to FIG. 6, the use of the pneumatic aspirating cutter 1100 for the minimally-invasive procedure for addressing otosclerosis (and other procedures) can also be combined with liquid infusion or flooding of the middle ear and/or outer ear canal 25. The pneumatic aspirating cutter 1100 can also have general utility in removing membranes and fibrous tissues in the middle ear.

In the case of the axially reciprocating blade of the inner reciprocating shaft 1120, the port defined by the outer shaft 1110 is most ideally located on the side of the outer shaft 1110 so that target tissue is approached with the side of the instrument tip ("side cutting"). For example, this orientation can be preferred when debriding the perimeter of a tympanic membrane perforation in preparation for graft placement or repair. A side cutting port can also be ideal for removal of cerumen from the wall of the ear canal 25.

Figure 16:
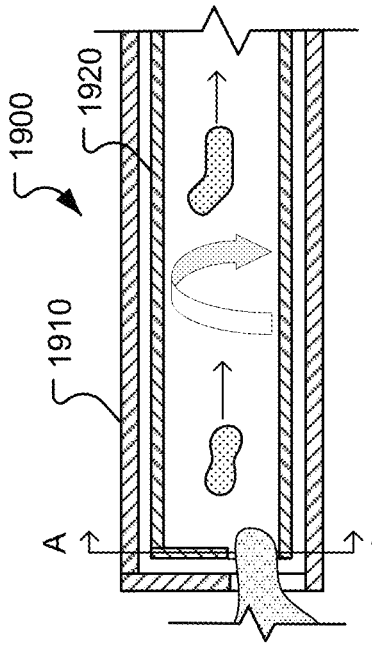
FIG. 16 illustrates the use of the cutting instrument of FIG. 15.
Figure 15:
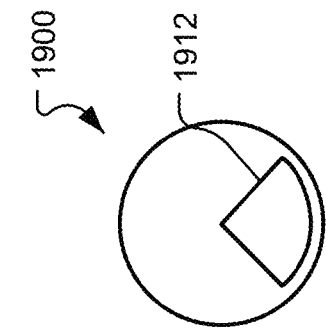
FIG. 15 is an end view of another example cutting instrument that can be used to perform various procedure described herein.
Figure 16A:
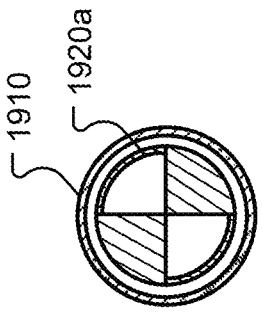
FIG. 16A illustrates an example cross-sectional view of the cutting instrument of FIG. 15.
Figure 16B:
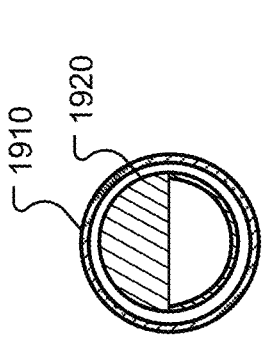
FIG. 16B illustrates another example cross-sectional view of the cutting instrument of FIG. 15.

FIGS. 15-16B depict another example high-speed cutter that can be used for the minimally-invasive procedure for addressing otosclerosis depicted in FIG. 6, and other otic procedures described herein. The rotary aspirating end cutter 1900 functionality can be combined with or incorporated in any of the otologic instruments described herein.

The high-speed rotary aspirating end cutter 1900 includes an outer shaft 1910 and an inner rotating shaft 1920. The inner rotating shaft 1920 rotates within the lumen defined by the outer shaft 1910. The end of the outer shaft 1910 defines an opening 1912 that can receive tissue therethrough. In the depicted embodiment, the opening 1912 is a circular segment (e.g., a quarter circle, semi-circle, etc.). Accordingly, as depicted in FIG. 16 tissue can be cut between the outer shaft 1910 and the inner rotating shaft 1920 (e.g., like a "rotary shearing" blade cutter) when the tissue is captured in the opening 1912. When portions of tissue are cut, the tissue portions can be aspirated through high-speed rotary aspirating cutter 1900 as shown.

The high-speed rotary aspirating end cutter 1900 can be useful, for example, for the minimally-invasive procedure for addressing otosclerosis depicted in FIG. 6, for removing middle ear soft tissue, cutting back the epithelial rim around the margins of a tympanic membrane perforation in a tympanoplasty procedure (e.g., the tympanic membrane repair procedure as described below), and the like. The high-speed rotary aspirating end cutter 1900 can also have general utility in removing membranes and fibrous tissues in the middle ear.

While the tip of the depicted high-speed rotary aspirating end cutter 1900 is blunt, in some embodiments the tip can be beveled, cone-shaped, radiused, and the like.

Removal of material (e.g., tissue, bone, etc.) can be conducted using high-speed rotary aspirating end cutter 1900. Cutting is achieved at the interface of the inner rotating shaft 1920 and the internal wall of the outer shaft 1910 at the location of the opening 1912. The shape and location of the opening 1912 can be configured for optimal contact with the target tissue or material. Since the cutting action occurs just within (approximately the wall thickness of the outer shaft 1910) the external surface of the instrument 1900, the size of the opening 1912 and the aspiration force can be selected to limit damage to the adjacent tissues while maximizing removal of target material. In some embodiments an aspiration channel down the center of the instrument 1900 can assist with pulling the target material into the opening 1912 to facilitate cutting. In some embodiments, the level of aspiration force and cutting speed of the instrument 1900 can be adjusted based on the mechanical properties of the target and surrounding tissues. Aspiration also enables immediate removal of cut or chopped material from the surgical field.

In some cases, such as removing material from bony surfaces of the middle ear for stapedotomy, it would be advantageous to have the cutting action located at the end of the instrument ("end cutting"), as provided by the high-speed rotary aspirating end cutter 1900. In such a case, a rotational blade is preferred. In this case, the instrument tip could be blunt, rounded, beveled, or cone shaped, with the cutting blade shape and orientation mirroring the shape and orientation of the opening 1912 to achieve an effective shearing or scissor-like cut.

FIG. 16B depicts an alternative inner rotating shaft 1920*a*. In this example, the inner rotating shaft 1920*a* has two end openings or cutting edges. The two end openings provide two tissue cuts per revolution (as compared to the single tissue cut per revolution provided by the inner rotating shaft 1920).

The high-speed rotary aspirating end cutter 1900 is appropriately sized for the application. In some embodiments, the outer diameter of the high-speed rotary aspirating end cutter 1900 would be in the range of 0.4 mm to 4 mm outer diameter, and preferably be less than 2 mm in diameter. The distal shaft portion that is inserted into the ear canal 25 would be 25-70 mm in length, preferably approximately 50 mm in length. The handle would preferably be smaller in diameter in order to not impede visualization of the target area. The handle can be at an angle or curve relative to the distal shaft, or the distal shaft itself can have a curve.

In some embodiments, the example instrument 400 for performing the minimally-invasive stapedotomy procedure (FIG. 6) and/or other otic procedures described herein, is an example coaxial bipolar diathermy instrument 1000 as shown in FIG. 11. The coaxial diathermy instrument 1000 includes a probe 1010 and a distal tip 1020 that includes an electrode to deliver heat. With the use of the coaxial principle, the current flows only at the probe's end surfaces. It allows a functionality that is essentially an intense heat to be localized at the very distal tip 1020 of the probe 1010. It's small size and end-on coagulation effect, and when used with a low-frequency diathermy unit, allow such a probe to be used safely in close proximity to delicate tissues. Bipolar diathermy instruments are used in the canal 25 and externally in otology but are, and previously have been, too large and imprecise for middle ear surgery. Extant diathermy instruments in the otology field have not been used in middle ear procedures for a variety of reasons, including the difficulty in access to the middle or inner ear region, and because of the bony structures of the middle ear blocking straight-line angle of attack to the desired target.

In some embodiments, the probe 1010 can be deflectable or steerable (as described above) for functionality off-axis. In other embodiments, an aspiration feature could be included in the same instrument to remove loose blood or thin clots from actively bleeding vessels, and then coagulate them immediately. This coaxial diathermy instrument 1000 is highly advantageous and enables a whole new functionality for otologic procedures.

FIG. 12 depicts an optional modification of the coaxial bipolar diathermy instrument 1000. Diathermy on its own is a useful modality for surgical intervention that is not currently used in otology; whether in mastoid/open access procedures, external ear canal 25, middle ear, or inner ear applications. The addition of other functionality to diathermy would increase the usefulness even further than expected.

One additional, useful functionality that can optionally be added to the coaxial bipolar diathermy instrument 1000 is adding lighting (as depicted by light rays 1022). The diathermy instrument 1000 can have a light source mounted at the distal tip, or a fiber optic that carries light to the distal tip. Adequate lighting can be problematic in otologic procedures, especially if the handles of the instruments in use are blocking a light source. The middle ear and surrounding anatomy are made up of many small complex structures that create corners that block visualization and lighting as well, and having on-board lighting with the diathermy probe instrument 1000 would greatly enhance its range of use as well as ease of use. The ability to control a light source proximal to the target tissue also minimizes the potential for glare created from reflection off other surfaces, such as the tympanic membrane. Movements of the light source during operation can also cast shadows, allowing for more ready identification of anatomic structures.

Another additional useful functionality that can optionally be added to the coaxial bipolar diathermy instrument 1000 is aspiration (as depicted by arrows 1024). Diathermy would likely be predominantly useful for controlling bleeds as a way to cauterize micro-vessels in the middle ear cavity or in the ear canal 25. Adding aspiration functionality would enable "one handed" ability to cauterize vessels while clearing out the surgical space of blood and other cauterized tissue. This two-part ability to manage bleeding would greatly ease the clinicians' ability to quickly control bleeds and thereby minimize procedure time, minimize instrument exchanges and associated risks of collateral tissue damage, reduce personnel required and number of hands in the surgical space, and overall ease a burdensome task encountered in most surgical procedures.

The use of the coaxial bipolar diathermy instrument 1000 in combination with built-in lighting 1022 and/or aspiration 1024 would create a one-handed instrument 1000 well suited to use in otologic procedures such as minimally-invasive stapedotomy and other procedures described herein with value greater than the expected sum of the individual functionalities.

Figure 7:
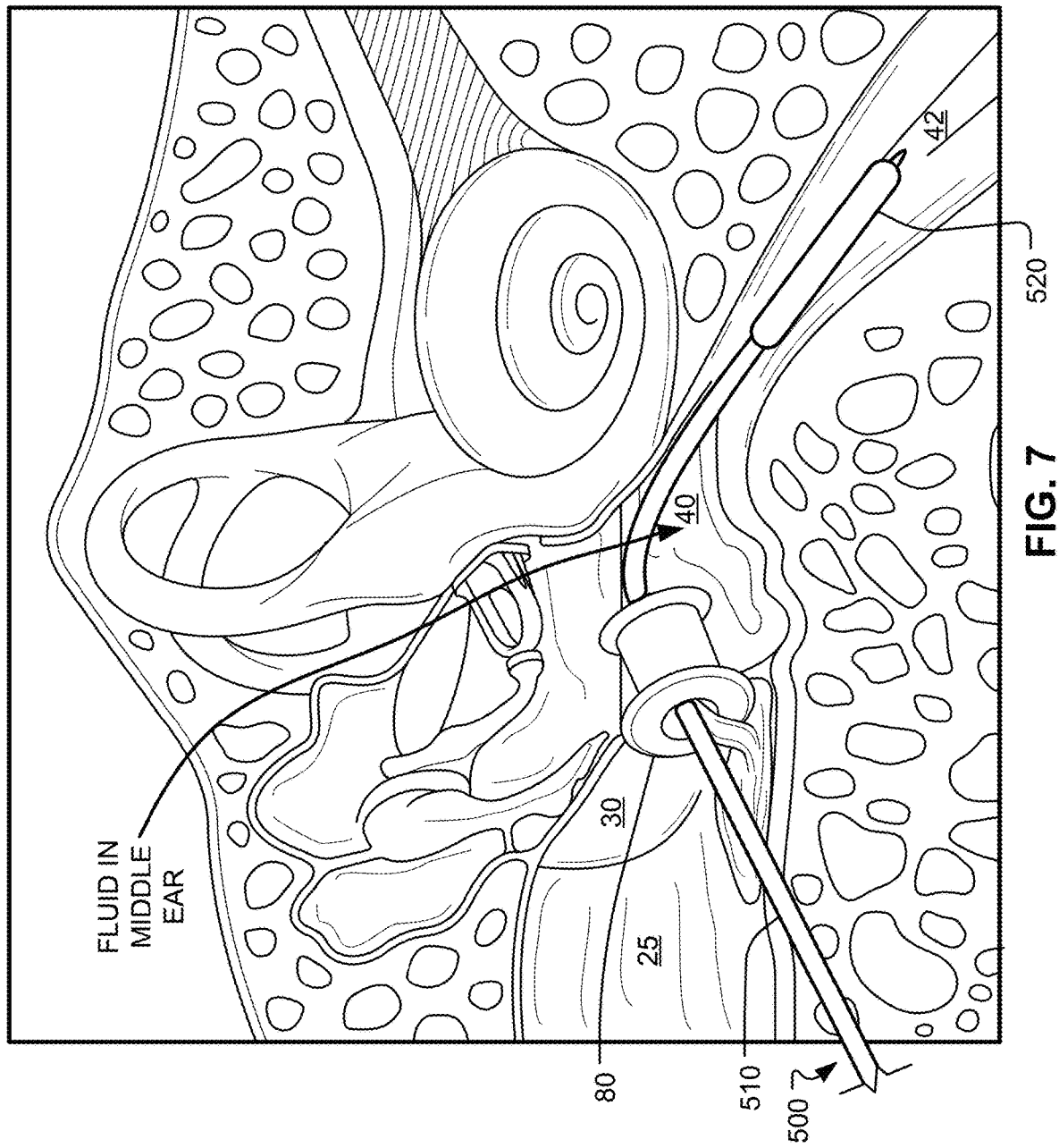
FIGS. 7 and 8 illustrate an example myringotomy procedure that can be performed with enhanced efficacy using the instruments and techniques described herein.
Figure 8:
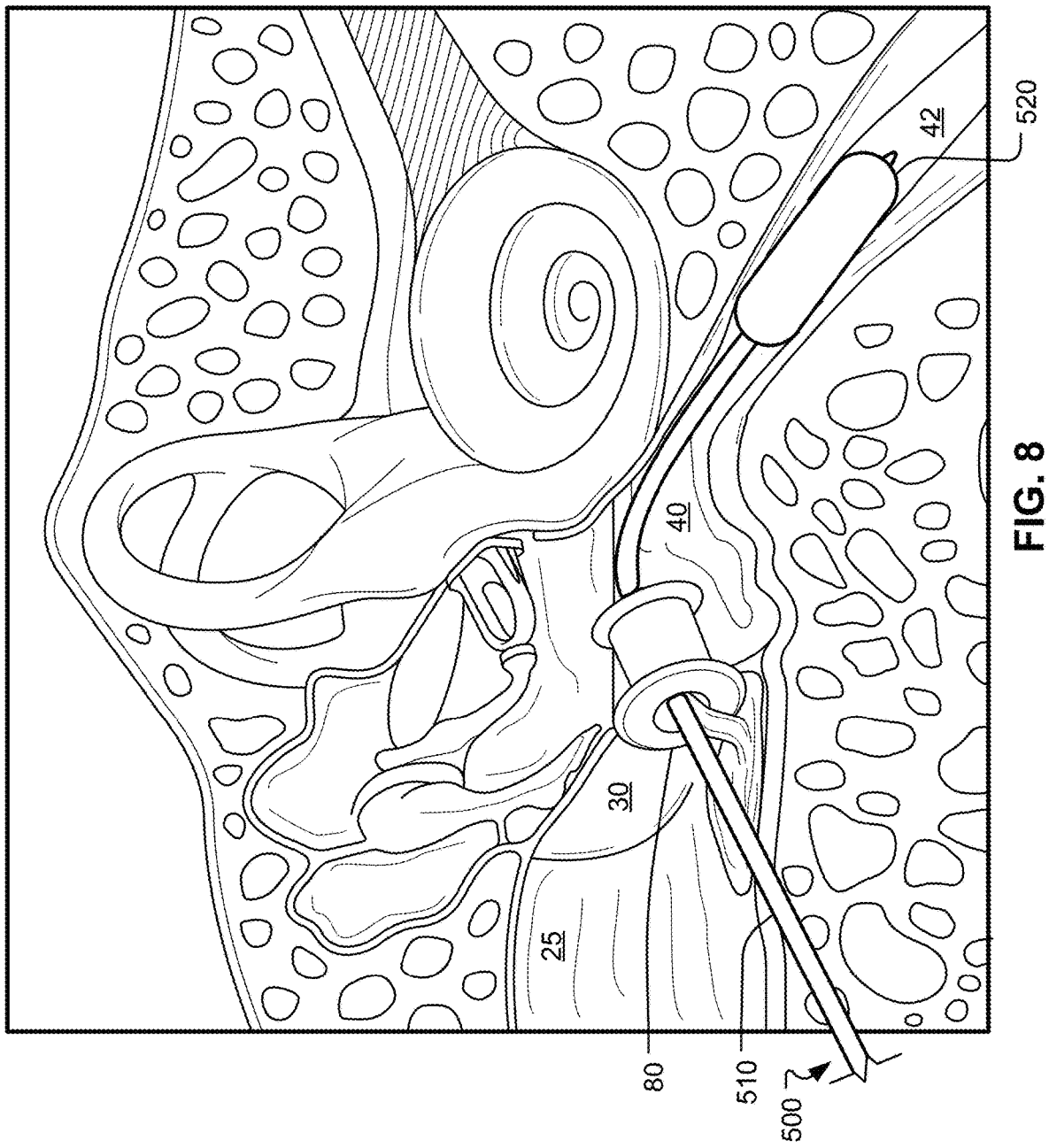

FIGS. 7-8 depict an example minimally-invasive Eustachian tube treatment technique in accordance with some embodiments. The proximity of the Eustachian tube 42 to the carotid arteries and other sensitive structures makes it potentially dangerous for surgery. Ear infections are an especially common issue, and the common treatment using myringotomy tubes 80 to create an opening of the tympanic membrane 30 is an imperfect solution to a fluid accumulation that is ultimately caused by Eustachian tube blockage. Accordingly, the depicted minimally-invasive Eustachian tube 42 treatment is an advantageous technique that can address the underlying cause of most ear infections. Additionally, using trans-canal 25 access, myringotomy ear drainage tube access, ports, or any of the minimally invasive access methods, can facilitate procedures that can be done in office settings without general anesthesia, an advantage that opens up the potential for the methods described. As another advantage, the access path is potentially much shorter and less tortuous, which dramatically reduces the difficulty in constructing delivery systems that can reach the target areas, in comparison to catheters that have to maneuver the tortuous and long nasopharyngeal approach. Being able to minimally invasively access the Eustachian tube 42 through a trans-canal 25 approach may be advantageous because it eliminates or reduces many of the delivery issues that have prevented most direct treatments of Eustachian tube 42 blockage or dysfunction from gaining traction, and enables new methods of targeted delivery directly to the Eustachian tube 42 and adjacent areas.

Here, a myringotomy ear drainage tube 80 (or a temporarily positioned TM port device 200 such as shown in FIGS. 4A-B), provides access through the TM 30 to the middle ear 40 (which is fluid-filled in this example). That is, a distal end portion of a balloon catheter device 500 can be extended into the middle ear 40, such that a balloon 520 of the balloon catheter device 500 is positioned in the Eustachian tube 42. During the advancement of the balloon catheter device 500, the balloon 520 is in a deflated condition. In particular, the deflated balloon 520 is positioned in a portion of the Eustachian tube 42 that is not bony (e.g., the elastic cartilaginous part of the Eustachian tube 42, i.e., the lower two-thirds that borders the nasopharynx).

In some embodiments, a distal tip portion of the balloon catheter device 500 is steerable to aid in the placement of the deflated balloon 520 in the Eustachian tube 42. With the deflated balloon 520 positioned in the Eustachian tube 42, the balloon 520 can be inflated to radially expand the balloon 520. The dilation of the Eustachian tube 42 resulting from the expansion of the balloon 520 stretches the lining of the Eustachian tube 42, leading it to heal with a thin layer of fibrous scar tissue that helps prop the Eustachian tube 42 open and increases the size of the lumen of the Eustachian tube 42, which is helpful for promoting drainage. In some embodiments, the balloon 520 can be drug-coated. In some embodiments, the balloon 520 can deliver a stent that holds the Eustachian tube 42 open. In some such embodiments, the stent can be a drug-eluting stent. In some such embodiments, the stent can be a bioresorbable stent. A stent can be a more durable solution to Eustachian tube blockage than myringotomy tubes 80.

The myringotomy ear drainage tube 80 (or a temporarily positioned TM port device 200 such as shown in FIGS. 4A-B) can be composed wholly or in part of resorbable materials, which would allow the tube or port to dissolve and/or fall out over time, minimizing the risk of tissue damage during physical removal. Resorbable materials can include examples such as polylactides and collagen scaffolds.

Figure 9:
FIG. 9 illustrates another example myringotomy procedure in accordance with some embodiments.

Referring to FIG. 9, in a similar access/approach manner (e.g., via the outer ear canal 25), the myringotomy ear drainage tube 80 (or a TM port device 200) creates ready access point for delivery of sprays, gels, therapeutics, gene delivery, antibiotics, anti-mucosal agents, surfactants, dilating agents or adrenaline, devices, and so on, to the middle ear 40 and/or Eustachian tube 42. A cannula or needle 600 can be used to deliver gel or liquid that could be loaded with antibiotics, antihistamines, decongestants, mucus thinners/expectorants, dilating agents or adrenaline, surfactants, etc. Such needles or cannulas 600 could integrate any/all features of the instruments described herein (e.g., a small gauge shaft, a flexible shaft, a steerable/deflectable shaft, an angulated shaft, a curved shaft, and/or combinations of functionalities including, but not limited to, aspiration, lighting, irrigation, endoscopy, diathermy, laser energy delivery, injection, ultrasound emulsification, and so on). As an example, a myringotomy ear drainage tube 80 (or a TM port device 200) allows for the direct intratympanic delivery of therapeutic treatments precisely to the tympanic end of the Eustachian tube 42 to treat Eustachian tube dysfunction. Precise delivery of therapeutics to the middle ear for the treatment of Eustachian tube dysfunction could be achieved with formulations including, but not limited to, surfactants like dipalmitoylphosphatidylcholine [DPPC], beractant, calfactant, poractant alfa, simethicone; betahistine, or others. As opposed to the well described intranasal approach to treating Eustachian tube dysfunction, middle ear 40 access provides access to a natural reservoir in the hypotympanum, and closer to the Eustachian isthmus or bony-cartilaginous junction, potentially allowing for longer sustained release of therapeutics to modify the surface tension of the Eustachian tube 42 and enhance its opening action so that ventilation of the middle ear can be restored.

Figure 10:
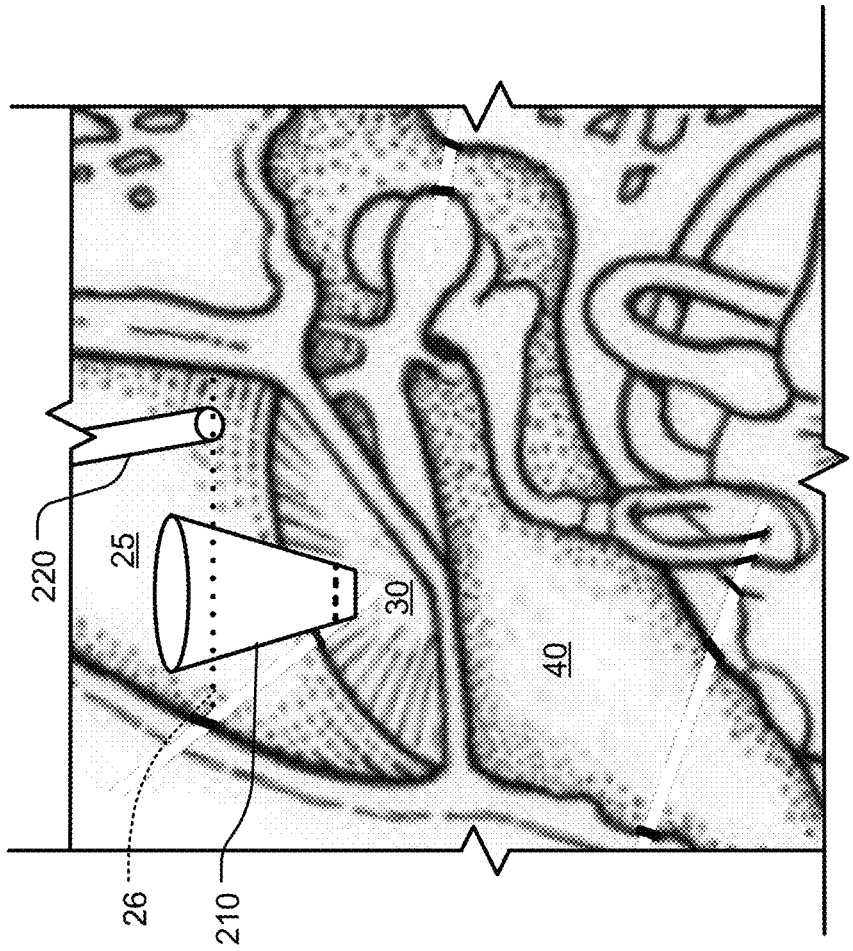
FIG. 10 illustrates another example technique for performing otic procedures with a fluid-filled space.

Referring to FIG. 10, in some embodiments the procedures described herein, and other otic procedures, can be performed advantageously by flooding the middle ear 40 and/or outer ear 25. The cavity of the middle ear 40 is normally filled with air. A liquid (e.g., saline, water, etc.) could be used to temporarily fill the cavity of the middle ear 40 such that treatment procedures described herein could be performed "underwater." This approach would confer a number of advantages.

When placing cochlear implant electrodes, the scala tympani, one of the fluid filled compartments of the cochlea, is intentionally breached. This can result in loss of perilymph fluid, which leaks into the air-filled middle ear 40, potentially leading to dizziness and/or permanent damage of the delicate cellular structures of the cochlea. Filling the cavity of the middle ear 40 with an artificial perilymph-like fluid (e.g. artificial cerebrospinal fluid with higher protein concentration) or a sodium hyaluronate-based viscoelastic (e.g., Healon, DuoVisc, ProVisc or Viscoat) could maintain fluid equilibrium in the cochlea during surgery.

When performing middle ear or inner ear surgery (e.g., cholesteatoma surgery or stapedectomy), the round window membrane or the oval window can be inadvertently disrupted, resulting in loss of perilymph fluid, which can leak into the air-filled middle ear 40, leading to dizziness and permanent damage of the delicate cellular structures of the cochlea. Filling the cavity of the middle ear 40 with an artificial perilymph-like fluid (e.g. artificial cerebrospinal fluid with higher protein concentration) or a sodium hyaluronate-based viscoelastic (e.g., Healon, DuoVisc, ProVisc or Viscoat) could maintain fluid equilibrium in the cochlea during surgery.

Creating a cochleostomy to place cochlear implant electrodes, to access the inner ear cavity for the treatment of neuromas, schwannomas, or for any other reasons, can result in loss of perilymph fluid, leading to dizziness and permanent damage of the delicate cellular structures of the cochlea. Filling the cavity of the middle ear 40 with an artificial perilymph-like fluid (e.g. artificial cerebrospinal fluid with higher protein concentration) or a sodium hyaluronate-based viscoelastic (e.g., Healon, DuoVisc, ProVisc or Viscoat) could maintain fluid equilibrium in the cochlea during surgery. Intraoperative hemorrhage in the middle ear space 40 must be constantly managed during surgical procedures. Maintaining a liquid filled compartment in the middle ear 40 could help to tamponade bleeding, particularly if a heavy liquid such as a sodium hyaluronate-based viscoelastic (e.g., Healon, DuoVisc, ProVisc or Viscoat) or silicone oil is used. Alternately the fluid could contain hemostatic agents to further reduce bleeding.

Maintaining a constant infusion of simple saline solution or artificial perilymph-like fluid in the middle ear 40 can allow for aspiration procedures to be performed which would allow for constant irrigation or washing of ear structures. The addition of antioxidant agents such as glutathione can also be added to the irrigation fluid to minimize intraoperative and post-operative inflammation. This can be beneficial in controlling bleeding and in allowing for the use of aspirating ultrasonic instruments for tissue removal and aspirating pneumatic cutters. These instruments can simultaneously provide infusion and aspiration, in some embodiments. Simultaneous infusion and aspiration would minimize the need for frequent instrument exchanges and allow for more efficient removal of blood and other debris. This exchange would be particularly beneficial in cholesteatoma removal, where complete removal of infiltrating epithelial tissue is critical for minimizing risk of recurrence.

An endoscope could be used to enable visualization of the liquid-filled middle ear 40. Using an endoscope in a liquid-filled space removes concerns or difficulties with fogging or blood obscuring the lens, and the associated subsequent need to clean the lens of the endoscope. Alternatively, a lens could be placed at the air/liquid interface to allow for visualization through the microscope (similar to a swimmer's mask). The lens could have ports through or around it to allow for instrument passage. In some embodiments, such a lens can be made to provide a wide viewing angle.

In the case of tympanoplasty, it may be advantageous to fill all or a portion of the ear canal 25 with fluid, in addition to the middle ear cavity 40. This would provide additional mechanical support to the tympanic membrane 30 and allow for an aspirating cutter to be used for trimming the margins of the perforation.

Still referring to FIG. 10, in the depicted example a TM port or lens assembly 210 is temporarily positioned in the TM 30. In some embodiments, the TM port or lens assembly 210 is a TM port 210. Alternately, in some embodiments the TM port or lens assembly 210 is a TM lens assembly 210 (for viewing into the middle ear 40).

The TM lens assembly 210 includes a frustoconical proximal portion that extends into the outer ear 25. In this example, the frustoconical proximal portion of the TM lens assembly 210 acts as a dam to allow partial flooding of the outer ear 25 (e.g., to the level 26) while ensuring the proximal surface of the TM lens assembly 210 remains dry. The use of the an open passage between the middle ear and external ear (either via an incision, an open or valved TM port 210, or other means) allows any excess fluid in the middle ear to exit without creating high pressure in the middle ear 40, and partially filling the ear canal 25 or a tubular member as overflow or excess thereby facilitates regulation of the liquid volume/pressure in the middle ear 40 without requiring additional potentially complex instrumentation. By controlling the fluid level in the canal 25 combined with this frustoconical feature, the lens/water interface on the lens distal surface and lens/air interface on proximal surface are maintained, allowing for optimal optical transmission to an externally-situated surgical microscope.

In some embodiments, the TM port or lens assembly 210 is a TM port for accessing the middle ear 40. The "walls" or "funnel" surrounding the TM port can be used in combination with a valved port to keep the proximal port surface dry. This has the advantage of preventing potential contamination of the middle ear irrigating fluid during instrument insertion through the port. Another advantage of maintaining dry TM port surfaces is to maintain visibility of the ports for ease of instrument targeting.

In some embodiments, an aspiration instrument 220 (or a speculum with an aspiration feature) is used in the outer ear 25 to control the level 26 of the liquid in the outer ear 25 (or to entirely remove liquid in the outer ear 25). The aspiration instrument 220 can be a wicking or typical suction-driven aspiration instrument.

In particular embodiments, the TM port 210 includes one or more valves to limit fluid egress into the outer ear 25. The TM port 210 can also include various valves/openings for ports for instruments, viewing, aspiration, irrigation, etc.

Conversely, the valve(s) could be unidirectional to limit fluid ingress into the middle ear 40 in order to allow fluid to exit the middle ear 40 and not return through the valve. As an example, this directs the flow of infusion fluid from the middle ear 40 to the canal 25, minimizing potential contamination of fluid in the middle ear 40 from fluid that has contacted the skin of the canal 25.

In another example embodiment, the TM port or lens assembly 210 can have one or more side channels to allow bi-directional flow and "venting" of excess fluid from the middle ear 40.

In another example embodiment, the TM port 210 can be connected to a predominantly tubular member that extends proximally outward from the port, and said tubular member can serve as the overflow reservoir for any excess fluid in the middle ear 40 to exit without creating high pressure in the middle ear 40, thereby facilitating regulation of the liquid volume/pressure in the middle ear 40 and obviating the need for valves or walls on other lenses or ports used during the same procedures. Such a tubular member can be connected to a side-flow or aspiration apparatus at a given height above the port site to thereby maintain a given pressure determined by the head height of the side-flow.

Although the Eustachian isthmus would likely be constricted for the duration of a fluid-filled procedure (the Eustachian tubes are typically closed except when chewing, swallowing, or yawning) and thereby enable fluid filling of the middle ear, it is envisioned that the instruments described herein (e.g., a small gauge shaft, a flexible shaft, a steerable/deflectable shaft, an angulated shaft, a curved shaft, and/or combinations of functionalities including, but not limited to, aspiration, lighting, irrigation, endoscopy, diathermy, laser energy delivery, injection, ultrasound emulsification, and so on) can enable localized delivery of agents (such as vasoconstrictors or prokinetic-like agents) to stimulate constriction of the Eustachian isthmus, and thereby enable fluid filling of the middle ear space. In other embodiments, the isthmus can be mechanically sealed, such as by a temporarily-deployed balloon catheter, or by a short-term resorbable gel (e.g., formulated to dissolve on an hours-long timescale).

Conversely, it is envisioned that it is in some cases advantageous to ensure the Eustachian isthmus is unconstricted or open to provide drainage of the middle ear space after a procedure using the fluid-filled approach. It is envisioned that the instruments described herein (e.g., a small gauge shaft, a flexible shaft, a steerable/deflectable shaft, an angulated shaft, a curved shaft, and/or combinations of functionalities including, but not limited to, aspiration, lighting, irrigation, endoscopy, diathermy, laser energy delivery, injection, ultrasound emulsification, and so on) can enable localized delivery of agents such as antibiotics, antihistamines, decongestants, mucus thinners/expectorants, dilating agents or adrenaline, surfactants, etc., to effect dilation or opening of the Eustachian isthmus and thereby facilitate fluid draining of the middle ear space.

Figure 13:
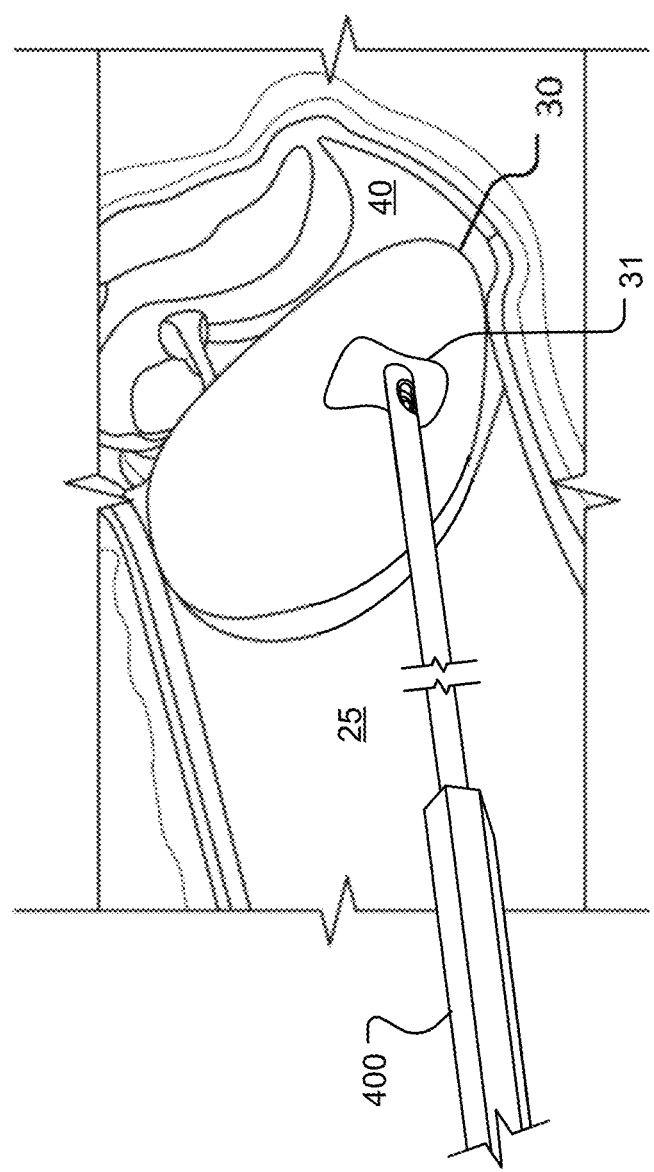
FIG. 13 illustrates an example tympanoplasty procedure in accordance with some embodiment.

FIG. 13 depicts an example tympanoplasty procedure using an example instrument 400. In some embodiments, the tympanoplasty procedure can be performed under-water.

During the tympanoplasty procedure, the margins of an existing tympanic membrane perforation 31 are first "freshened" by removing tissue around the perimeter of the perforation 31. Currently there is no precise instrument for performing this procedure, and typically more tissue is removed than necessary, further enlarging the perforation, complicating the subsequent patching procedure, and reducing the chance of successful closure of the perforation 31.

In some cases, the example instrument 400 used for performing the tympanoplasty procedure can be the small pneumatic "guillotine" blade cutter with aspiration provided by the pneumatic aspirating cutter 1100 (FIG. 14). The pneumatic aspirating cutter 1100 can ensure more precise cutting of the perimeter of the perforation 31 because the TM 30 can be held in tension by the aspiration force during the cutting. Further, the cutting action does not require hand actuation, as with a scissor, so that precision cuts can be controlled simply by guiding the location of the instrument cutting port to the target tissue. Thus, the small pneumatic "guillotine" blade cutter with aspiration provided by the pneumatic aspirating cutter 1100, can ensure more precise cutting of the perimeter of the perforation 31. In some embodiments, this cutting can also be combined with liquid infusion or flooding of the middle ear 40 and/or outer ear canal 25. The pneumatic aspirating cutter 1100 can also have utility in removing membranes and fibrous tissues in the middle ear 40.

Various other types of instruments 400 can be used for the tympanoplasty procedure. For example, in some embodiments an ultrasound instrument, a scraper, or the end cutter (FIG. 15-16B) can be used to remove epithelial surface tissue around the perimeter of the perforation 31.

While the instruments disclosed herein are primarily described in the context of otologic procedures that are either in the outer ear or that use a trans-canal, trans-tympanic membrane approach to the middle ear or inner ear, it should be understood that the instruments are not limited to such uses, and could be used for other cavities or spaces in the body and other approaches. For example, in some embodiments the instruments described herein can be used for other approaches and techniques to the middle ear, inner ear, Eustachian tube, mastoid antrum space including, but not limited to, trans-mastoid access, trans-canal via tympanomeatal flap, trans-tympanic membrane annulus, endaural, retroaural, postaural, and others. Such systems and methods can be used for drug delivery, gel delivery, antibiotic delivery, gene delivery, graft placement, device or implant delivery, tissue removal, diagnostic procedures, sampling procedures, surgical procedures, among others.

It should be noted that any of the embodiments or features of embodiments described herein can be combined in any combinations and any permutations, and all are within the scope of this disclosure.

The devices, systems, and methods described herein may be used in the course of treating any disorder of the middle ear and/or inner ear including, but not limited to, hearing loss, tinnitus, balance disorders including vertigo, Meniere's Disease, vestibular neuronitis, vestibular schwannoma, labyrinthitis, otosclerosis, ossicular chain dislocation, cholesteatoma, otitis media, middle ear infections, and tympanic membrane perforations, to provide a few examples. In some embodiments, the devices, systems, and methods described herein may be used in the course of precise delivery of therapeutic agents to the round window niche and/or other target sites, such as the oval window or other parts of the middle ear cavity, and for providing access to other features or regions of the middle ear. For example, the systems and methods described herein can be used for minimally invasive surgical reconstruction of the ossicular chain, for removal of cholesteatoma, for diagnostic assessment, and other procedures. Any and all such techniques for using the systems and methods described herein are included within the scope of this disclosure.

The devices and systems described herein may be constructed of metals such as but not limited to aluminum, titanium, stainless steel, etc., or of polymers such as but not limited to ABS, PEEK, PET, HDPE, etc., injection molded components, and so on. Components, such as the flexible rings can be constructed of elastomeric materials, gels, etc.

The devices, systems, materials, compounds, compositions, articles, and methods described herein may be understood by reference to the above detailed description of specific aspects of the disclosed subject matter. It is to be understood, however, that the aspects described above are not limited to specific devices, systems, methods, or specific agents, as such may vary. It is also to be understood that the terminology used herein is for the purpose of describing particular aspects only and is not intended to be limiting.

A number of embodiments have been described. Nevertheless, it will be understood that various modifications may be made without departing from the claim scope here. Accordingly, other embodiments are within the scope of the following claims.

What is claimed is:

1. A method for treating cholesteatoma in a middle ear, the method comprising:
   advancing, via an outer ear canal and a trans-tympanic membrane approach into the middle ear, a shaft of an instrument through a lumen in the tympanic membrane having an access diameter of 0.5 mm to 1.0 mm such that a distal tip of the instrument comes into contact with the cholesteatoma in the middle ear at a location spaced posteriorly away from a Eustachian tube, wherein the instrument is configured to provide a combination of injection and ultrasound emulsification;

while at least a portion of the shaft of the instrument is positioned in the lumen in the tympanic membrane having the access diameter of 0.5 mm to 1.0 mm, delivering a therapeutic treatment that includes both a therapeutic agent injection and ultrasound emulsification from the distal tip of the instrument to the cholesteatoma to debulk the cholesteatoma via the trans-tympanic membrane approach at a first time; and after said delivering the therapeutic treatment that includes both the therapeutic agent injection and ultrasound emulsification to debulk the cholesteatoma at the first time, advancing at a second later time, a subsequent instrument through a subsequent lumen in the tympanic membrane having an access diameter of 0.5 mm to 1.0 mm such that a distal tip of the subsequent instrument comes into contact with a regrowth of the cholesteatoma in the middle ear at the location spaced posteriorly away from the Eustachian tube; and while at least a portion of the shaft of the subsequent instrument is positioned in the subsequent lumen in the tympanic membrane having the access diameter of 0.5 mm to 1.0 mm, delivering a subsequent therapeutic treatment that includes both a subsequent therapeutic agent injection and ultrasound emulsification from the distal tip of the subsequent instrument to the cholesteatoma to debulk the cholesteatoma via the trans-tympanic membrane approach at the second later time.

2. The method of claim 1, wherein the advancing at said first time comprises moving the shaft of the instrument through a perforation in the tympanic membrane.

3. The method of claim 2, further comprising placing a port device in the perforation in the tympanic membrane such that the port device defines the access diameter of 0.5 mm to 1.0 mm.

4. The method of claim 1, wherein the shaft of the instrument at the first time is configured to advance through the lumen in the tympanic membrane having the access diameter of 0.5 mm to 1.0 mm and comprises a steerable or deflectable shaft.

5. The method of claim 4, wherein the therapeutic agent injected into the cholesteatoma at the first time via the trans-tympanic membrane approach comprises a sustained release formulation.

6. The method of claim 5, wherein the therapeutic agent injected into the cholesteatoma at the first time via the trans-tympanic membrane approach comprises a keratolytic agent, an immune response modifier, or a cryotherapy agent.

7. The method of claim 6, wherein the therapeutic agent injected into the cholesteatoma at the first time via the trans-tympanic membrane approach is administered in combination with said ultrasound emulsification for tissue removal in the middle ear.

8. The method of claim 4, wherein said delivering the subsequent therapeutic treatment that includes both the subsequent therapeutic agent injection and ultrasound emulsification at the second later time is one or more years after the first time.

9. The method of claim 1, wherein the instrument is configured to provide a combination of endoscopy, injection, and ultrasound emulsification.

10. The method of claim 1, further comprising providing visual confirmation of the cholesteatoma in the middle ear prior to patient reported symptoms.

* * * * *